(12) United States Patent
Ryan et al.

(10) Patent No.: US 8,245,440 B2
(45) Date of Patent: Aug. 21, 2012

(54) AQUACULTURE RACEWAY INTEGRATED DESIGN

(75) Inventors: Randy D. Ryan, Tucson, AZ (US);
Peter M. Waller, Tucson, AZ (US);
Murat Kacira, Tucson, AZ (US);
Peiwen Li, Oro Valley, AZ (US)

(73) Assignee: The Arizona Board of Regents on Behalf of the University of Arizona, Tucson, AZ (US)

( * ) Notice: Subject to any disclaimer, the term of this patent is extended or adjusted under 35 U.S.C. 154(b) by 248 days.

(21) Appl. No.: 12/824,106

(22) Filed: Jun. 25, 2010

(65) Prior Publication Data
US 2011/0023360 A1    Feb. 3, 2011

Related U.S. Application Data

(60) Provisional application No. 61/269,585, filed on Jun. 26, 2009.

(51) Int. Cl.
*A01G 31/00* (2006.01)
*A01G 7/00* (2006.01)
*A01H 13/00* (2006.01)

(52) U.S. Cl. .......................................... 47/62 C; 47/1.4
(58) Field of Classification Search .................. 47/1.4, 47/59 R, 62 C
See application file for complete search history.

(56) References Cited

U.S. PATENT DOCUMENTS

| 5,981,271 | A | 11/1999 | Doucha et al. |
| 7,258,790 | B2 | 8/2007 | Brune et al. |
| 2008/0009055 | A1 | 1/2008 | Lewnard |
| 2008/0086939 | A1* | 4/2008 | Dunlop et al. ................... 47/1.4 |
| 2008/0155890 | A1 | 7/2008 | Oyler |
| 2008/0220515 | A1 | 9/2008 | McCall |
| 2009/0113790 | A1 | 5/2009 | Erd |
| 2009/0126265 | A1 | 5/2009 | Rasmussen et al. |
| 2009/0126269 | A1 | 5/2009 | Wilson et al. |
| 2009/0151240 | A1 | 6/2009 | Kayama et al. |
| 2011/0287544 | A1* | 11/2011 | Berzin et al. .................. 435/410 |

FOREIGN PATENT DOCUMENTS
WO    WO 2008/051865    5/2008

OTHER PUBLICATIONS

Setlik et al., "Dual purpose open circulation units for large scale culture of algae in temperate zones. I. Basic design considerations and scheme of pilot plant," *Algol. Stud. (Trebon)*, vol. 1, pp. 111-164, 1970.

* cited by examiner

*Primary Examiner* — Monica Williams
(74) *Attorney, Agent, or Firm* — Klarquist Sparkman, LLP

(57) ABSTRACT

Disclosed herein are systems and methods for aquaculture. In one embodiment, the system includes a plurality of cultivation areas, a collection area, a pump for returning the culture from the collection areas to at least one of the cultivation areas and a delivery system for providing gases and/or nutrients to the culture. Also disclosed is a method for regulating water temperature of an aquaculture including circulating a culture through a system described herein, and storing the culture in the collection area or at least one of the cultivation areas for at least a portion of a 24 hour period.

23 Claims, 21 Drawing Sheets

AQUACULTURE RACEWAY INTEGRATED DESIGN

CROSS REFERENCE TO RELATED APPLICATION

This claims the benefit of U.S. Provisional Application No. 61/269,585, filed Jun. 26, 2009, which is incorporated herein in its entirety.

FIELD

This disclosure relates to aquaculture, particularly systems and methods for algae culture.

BACKGROUND

Biofuels are an alternative to conventional fossil fuels. However, one of the main drawbacks to conventional biofuel crops, such as corn, canola, sweet sorghum, etc., is their demand on land and water, and the fact that they shift resources from food production to fuel production. One solution is to develop production of biofuel feedstocks from resources that do not place a higher demand on agricultural land and resources, such as algae. Algae may ultimately be the preferred plant for biofuel production as an alternative to petrochemical replacements and also to conventional biofuel crops. However, at present, high capital and operation costs have been significant limitations for commercial production of biofuels from algae.

Over the past decade, researchers have focused on new algae production systems (photobioreactors) as an improvement over open pond and raceway systems. However, both types of systems have significant disadvantages and a need remains for effective and economical systems and methods for algae cultivation.

SUMMARY

One limitation of open raceway aquaculture systems is the temperature variation under variable climatic conditions. Disclosed herein are systems for aquaculture that allow simple and cost-effective regulation of water temperature within a range suitable for culture growth (for example, algae culture, such as *Botryococcus braunii*). In some embodiments, the system includes a plurality of cultivation areas including at least a first cultivation area and a second cultivation area, each cultivation area including an upper end and a lower end, wherein the upper end and lower end are substantially parallel, and a bottom surface comprising a liner; a collection area below the lower end of at least one of the plurality of cultivation areas; a pump for returning the culture from the collection area to the upper end of at least one of the plurality of cultivation areas; and a delivery device for providing gases (e.g., carbon dioxide) and/or nutrients to the culture. In particular examples, at least a portion of at least one of the plurality of cultivation areas or the collection area is adjacent to (for example, directly or indirectly in contact with) the ground (such as soil).

In some embodiments, a system also includes a canal that is substantially parallel to the upper end of at least one of the plurality of cultivation areas, wherein the culture is introduced into the upper end of at least one cultivation area from the canal (for example, from at least one opening along the length of the canal). In further embodiments, a system also includes a pipe (such as a return pipe or trough) that delivers the culture from the collection area to the canal, for example by being pumped from the collection area by the pump. In additional embodiments, a system also includes at least one sensor to monitor one or more parameters of the culture or the environment, and the system may also include a data acquisition system for collecting data from the at least one sensor.

Also disclosed is a method for regulating water temperature of an aquaculture utilizing a system described herein. In one embodiment, the method includes circulating a culture through a disclosed system and storing the culture in the collection area and/or at least one cultivation area for at least a portion of a 24 hour period, thereby regulating the water temperature of the culture. In one example, the water temperature is maintained at or above a minimum (for example, about 15° C.) by storing the culture in the collection area for at least a portion of a 24 hour period (for example, during a period of lower relative solar radiation, such as a period substantially lacking solar radiation). In other examples, the water temperature is increased by circulating the culture through the system in the presence of solar radiation. In further examples, the water temperature is decreased by circulating the culture through the system during a period of lower relative solar radiation (such as a period substantially lacking solar radiation). In some examples, the disclosed method maintains the water temperature between about 15° C. and about 35° C.

The foregoing and other features of the disclosure will become more apparent from the following detailed description, which proceeds with reference to the accompanying figures.

DETAILED DESCRIPTION

Figure 1:
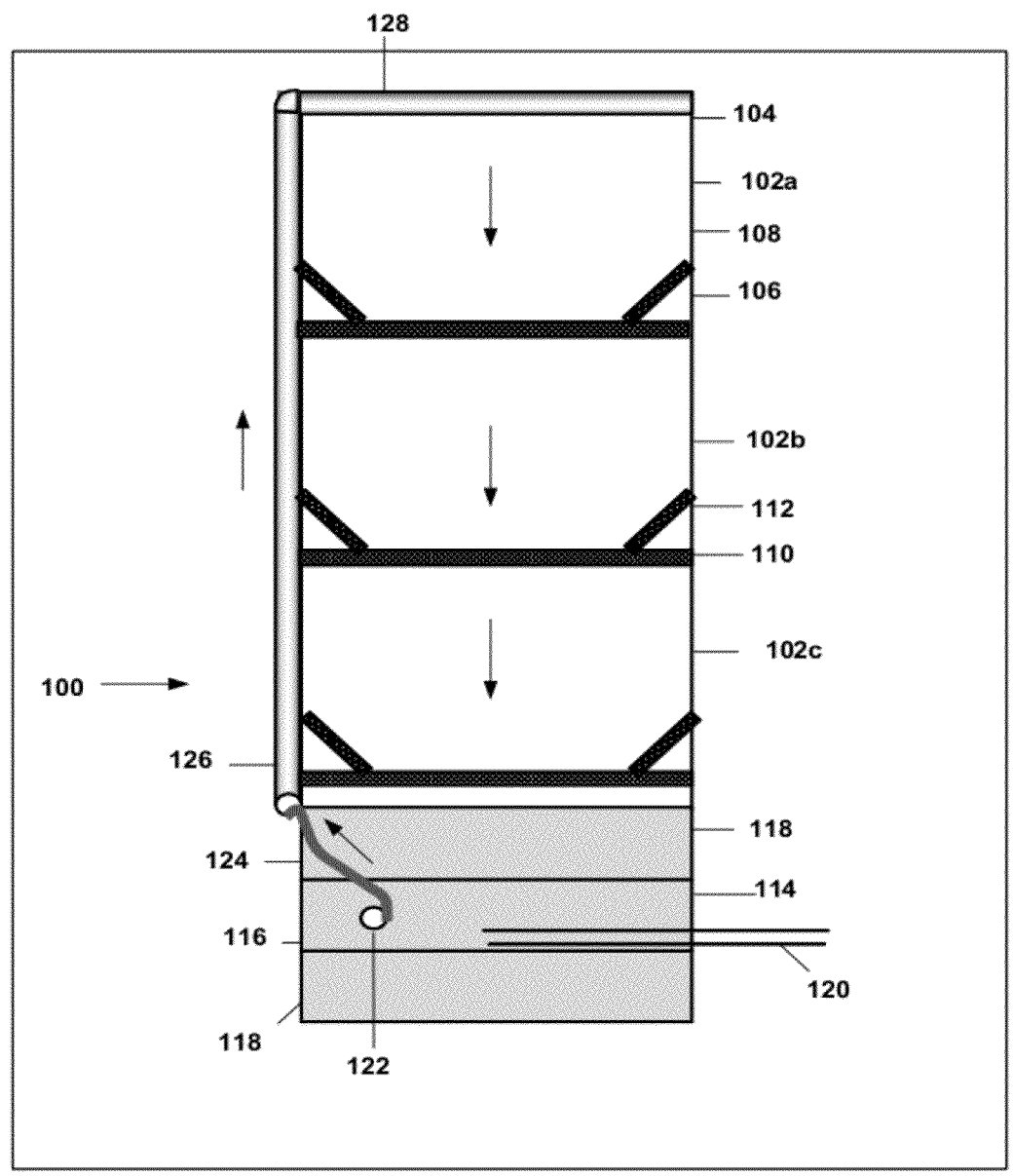
FIG. 1 is a top view of an exemplary embodiment of a system for aquaculture disclosed herein.

Recent efforts in algae culture have focused on photobioreactors, rather than open pond or raceway systems. Although each type of system has pros and cons, open raceway systems remain the most economical. The main drawbacks of open raceways are temperature variation under variable climatic conditions and competition by invaders to the preferred algae. In some examples, photobioreactors may provide more precise control of nutrients, pH, salinity, light intensity, and $CO_2$. However, significant advantages of open raceways include lower capital and operation costs, greater adaptability to poor water sources such as wastewater and high salinity water, and greater surface area and utilization of sunlight.

The Arid Raceway Integrated Design (ARID) system disclosed herein provides temperature control in arid conditions at an extremely low cost. In some examples, no waste heat or covering of the ARID raceway is required to maintain water temperature between 20° C. and 28° C. during the coldest winter months in the Southern Arizona desert region, for instance. The disclosed system can also be used to regulate water temperature in temperate climates.

The ARID system uses a unique design and method to empty and fill sections of an aquaculture raceway in order to control long wave radiation, heat transfer, solar radiation, and evaporation. The system also utilizes the underlying soil to strategically store energy or remove energy from the water. Controlling the components of the energy balance in this way during day and night allows maintenance of water temperature within the optimal range. The design can also be used to maximize light exposure of the culture in winter by flooding the entire system during the day.

Although a system and method are described herein primarily with respect to algae culture (for example, the culture of microalgae), the disclosed system and method in their several embodiments are also suitable for culture of other photosynthetic cells, including for example, cyanobacteria. The system and method are also suitable for aquaculture of other organisms, such as fish, shellfish, crustaceans, echinoderms, higher plants (for example, duckweed or kelp), fungi, bacteria, viruses (such as algae, plant, bacterial, or fungal viruses), and mixed cultures (for example, fish and algae).

I. Overview of Several Embodiments

Disclosed herein is a system for aquaculture (for example, algae culture) that maintains the water temperature within acceptable limits for the cultured organism during both the coldest winter months and the hottest summer months.

In some embodiments, a system includes a plurality of cultivation areas, each of which include an upper end and a lower end, wherein the upper end and the lower end are substantially parallel, and a bottom surface including a liner. The system also includes a collection area below the lower end of at least one of the plurality of cultivation areas, a pump for returning the culture from the collection area to the upper end of at least one of the plurality of the cultivation areas, and at least one delivery device for providing gas (e.g., carbon dioxide) and/or nutrients to the culture.

Each of the plurality of cultivation areas includes an upper end and a lower end, wherein the upper end has a higher bottom surface elevation than the lower end, produced by a downward slope from the upper end to the lower end. In some examples, the downward slope is at least about 0.1% (such as at least 0.2%, 0.3%, 0.4%, 0.5%, 0.6%, 0.7%, 0.8%, 0.9%, 1%, 2%, 3%, 4%, or 5%). In other examples, the slope is from about 0.1%-5% (for example, about 0.1%-4%, about 0.5%-4%, about 1%-4%, about 2%-4%, about 0.5%-2%, or about 0.5%-1.5%). In some examples, the slope is from about 0.5%-2%, such as about 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, or 2.0%. In a particular example, the downward slope from the upper end to the lower end is about 1%. The shape of the cultivation areas can be selected by one of skill in the art, and can include any shape (for example, the cultivation areas can be square, rectangular, circular, hexagonal, or any convenient shape).

Each of the plurality of cultivation areas also includes a bottom, which comprises a liner. The liner provides a substantially impermeable barrier that contains the culture in the ARID system. The liner can be any suitable material, such as polyethylene or other suitable polymer (such as high density polyethylene, low density polyethylene, linear low density polyethylene, chlorosulfonated polyethylene, polyvinyl chloride, polypropylene, ethylene propylene terpolymer, and ethylene interpolymer alloy). In some examples, the liner is about 5-100 mm thick (for examples, about 10-100, 20-80, 30-75, 20-60, or 10-50 mm). In one example, the liner is about 10, 20, 30, 40, or 50 mm thick, for example, about 30 mm thick. In a particular example, the liner is 30 mil thickness linear low density polypropylene (e.g. Aquafarm E-300, Colorado Lining International, Parker, Colo.).

In some examples, the liner extends from the bottom of the cultivation areas to cover one or more sides of the cultivation area (for example, the upper end, lower end, left side, and/or right side), and may also cover the bottom and/or sides of the collection area. In one example, the liner is a continuous piece of (for instance, black) polypropylene that lines the bottom and sides of each cultivation area and the bottom and sides of the collection area. It is not essential to the function of the system that the liner be continuous, but rather that it be sufficient to substantially contain the culture medium.

Selection of the color of the liner can be influenced according to the weather conditions (such as latitude and/or season). In some examples, the liner is a dark color that absorbs solar radiation (for example, black). In other examples, the liner is a light color that reflects solar radiation (for example, white). In particular examples, an absorptive (e.g., black) liner is used in the winter season or in temperate climates with cooler daytime temperatures, in order to maximize heat absorption by the system and maintain the culture at or above a desired minimum temperature. In other particular examples, a reflective (e.g., white) liner is used in the summer season or in arid and/or hot climates with warmer daytime temperatures, in order to minimize heat absorption by the system and maintain the culture at or below a desired maximum temperature.

A system disclosed herein also includes a collection area below (having a lower bottom surface and/or water surface elevation than) the lower end of at least one of the plurality of cultivation areas. In some embodiments, the collection area is located so that culture flows from a single cultivation area into the collection area. In other embodiments, the collection area is located so that culture flows from two or more cultivation areas into the collection area. The volume of the collection area is at least equal to the combined volume of the plurality of cultivation areas, such that the entire volume of culture in the system can be held in the collection area, leaving the cultivation areas substantially empty, or the entire volume of culture can be held in the cultivation areas, leaving the collection area substantially empty. In some examples, the volume of the collection area is at least equal to the total volume of the plurality of cultivation areas and any piping of the system. In other examples, the volume of the collection area is at least equal to the total volume of the culture in the plurality of cultivation areas and any piping of the system.

The shape of the collection area can be selected by one of skill in the art, and can include any shape (for example, the collection area can be square, rectangular, circular, hexagonal, or any convenient shape). In some non-limiting examples, at least one side (such as at least 2, 3, 4, or more sides) of the collection area is sloped, such that the collection area is wider at the top than at the bottom. Sloped sides are not required, but provide advantages, such as ease of construction and safety considerations. In some examples, the collection area has two sloped sides that are opposite one another. In further examples, each of the sloped sides has a substantially equal slope. The slope can be about 0.5:1 to about 2:1 (such as about 1:1 to about 1.5:1). In a particular example, the slope of each sloped side is about 1:1.

The system includes a pump or other water displacement member for returning the water/culture from the collection area to the upper end of at least one of the plurality of cultivation areas. In some examples, the pump or displacement member includes an airlift pump, an axial flow pump, a centrifugal pump, a screw pump, a propeller pump, or a positive displacement pump. In other examples, the pump or displacement member includes a water wheel mechanism for lifting the culture or water. In some embodiments, the pump returns the culture to the upper end of a single cultivation area. In other embodiments, the pump returns the culture to the upper end of two or more cultivation areas.

A disclosed embodiment of the system also includes at least one delivery device for providing carbon dioxide, air, other gases, and/or nutrients to the culture. In some examples, the at least one delivery device is placed in the collection area, the canal, at least one of the plurality of cultivation areas, or a combination of two or more thereof. In some examples, the delivery device includes one or more carbon dioxide diffusers. In other examples, the delivery device includes one or more pipes for delivery of nutrients, for example a solution including salts (such as one or more of $KNO_3$, $K_2HPO_4$, $CaCl_2$, $MgSO_4$, $CoCl_2$, $H_3BO_3$, $MnCl_2$, $ZnSO_4$, $CuSO_4$, $Na_2MoO_4$, $H_2SO_4$, or citric acid) or other beneficial nutrients. In one example, a carbon dioxide and/or air delivery device is included in the collection area. One of skill in the art can select appropriate nutrients and concentrations based on the organisms present in the ARID system.

In some embodiments, at least a portion of at least one of the plurality of cultivation areas and/or the collection area is adjacent to the ground (such as soil). Contact with the ground (such as direct or indirect contact with soil) provides a thermal mass that can regulate water temperature in the system. In some examples, the ground (such as soil) acts as an insulator, for example, reducing heat loss by the water in the system. In other examples, the ground acts as a heat sink, for example, absorbing heat from the water in the system. In particular examples, at least a portion of the cultivation areas and/or the collection area are directly adjacent to the ground (for example, in direct contact with soil). For example, in some embodiments, at least one of the cultivation areas and/or collection area are constructed by excavating an area in the soil, and the cultivation area and/or collection area is defined by a liner (such as a plastic liner) that is laid in contact with the soil. In some examples, at least the bottom surface of the plurality of cultivation areas is directly in contact with soil. In further examples, the bottom surface and sides of the plurality of cultivation areas is directly in contact with soil. In additional examples, the bottom surface and sides of the collection area is directly in contact with soil. In a particular example, the bottom surface and sides (e.g., the liner) of each of the plurality of cultivation areas and the collection area are in direct contact with the ground (for example, the cultivation areas and collection area are excavated in the soil).

In other examples, at least a portion of at least one of the cultivation areas and/or the collection area is not directly adjacent to (in contact with) the ground; instead, the cultivation areas and/or collection area are indirectly adjacent to the ground, but is/are still thermally affected by the ground. In some examples, a low thermal conductivity material is present between at least a portion (for example, the bottom surface and/or one or more sides) of at least one cultivation area and/or the collection area and the ground (for example, soil). Placing a low thermal conductivity material between the cultivation areas and/or collection area and the ground can reduce thermal conductivity from the soil to the cultivation area and or the collection area (such as the liner), thereby reducing heat loss or gain of the culture from the ground. In some examples, the low thermal conductivity material includes straw, dry sand, foam (such as polystyrene or polyethylene), textile materials (for example, carpeting), cellular cushioning packaging material (for example, BUBBLE WRAP®), air (such as air contained in a non-radiative liner), or a combination of one or more thereof. In some embodiments (such as in an arid and/or hot climate), a low thermal conductive material is placed between at least one cultivation area and/or the collection area and the ground (such as soil) during cool (e.g., winter) months and at least one cultivation area and/or the collection area is directly adjacent to the ground (such as soil) during warm (e.g., summer) months.

In other examples, a radiant barrier is created by placing a reflective material (such as foil or MYLAR®) between the liner and the ground. In some examples, an air gap is created between the liner and the reflective material by injecting air (for example, from a pneumatic device) below the liner when the cultivation area is drained of water and/or culture. In this case, the water is in direct thermal contact with the soil when the cultivation area is filled with water, but there is a thermal barrier (air gap and no radiation) between the soil and atmosphere when the cultivation area is drained of water and/or culture. This can prevent the soil from losing energy at night and/or taking energy out of the water when the cultivation areas are refilled.

In other examples, a temperature regulation device is present between at least a portion (for example, the bottom surface and/or one or more sides) of at least one cultivation area and/or the collection area and the ground (such as in water or a soil layer). In some examples, the temperature regulation device includes at least one heating pipe. In some examples, heat for the heating pipe is waste heat, for example from a biogasification system, solar cell waste heat unit, power plant, geo-thermal source, or industrial plant located near the system. In other examples, heat for the heating pipe is provided from warm water. In further examples, the temperature regulation device includes at least one cooling pipe, such as a pipe for circulating cool water. In further examples, the temperature regulation device includes a bladder system (such as one or more bladders) filled with a fluid (such as water) or a gel. The temperature of the fluid or gel in the bladders can be heated or cooled, for example by a heater.

In some embodiments, a system includes a canal that is substantially parallel to the upper end of at least one of the plurality of cultivation areas and has a bottom surface elevation that is higher than the upper end of at least one of the plurality of cultivation areas. In some examples, the canal is at least partially open, such as a trough. In other examples, the canal is substantially closed, for example, a pipe. In some examples, the canal is a pipe with a diameter of at least about 4 inches (such as about 4, 5, 6, 7, 8, 9, 10, 11, 12, 13, 14, 15, 16, 17, 18, 19, 20, 21, 22, 23, or 24 inches). For example, the canal can have a diameter of about 2-30 inches (such as about 6-24 inches, 8-16 inches, 4-18 inches, or 8-18 inches). In a particular example, the diameter of the canal is about 12 inches. In other examples, the canal is a trough with a depth of about 2-18 inches (such as about 2-16 inches, 4-16 inches, 6-12 inches, 6-18 inches, or about 6 inches).

The canal is connected to the collection area by a return trough or pipe, along which the culture is pumped from the collection area to the canal. The canal includes a first end (for example, connected to the return pipe) and a second end. In some examples, the first end is open and the second end is closed. In other examples, the first end is open and the second end is also open, such that at least some of the culture flows directly to the collection area (for example, via a separate channel), rather than flowing through the cultivation areas.

The canal also includes at least one opening along the length of the canal, allowing the culture to be introduced to the upper end of at least one of the plurality of cultivation areas. In some examples, the canal includes multiple openings or groups of openings along the length of the canal, allowing exit of the culture into the upper end of one or more cultivation areas. In a particular example, the canal includes at least two openings (such as at least 3, 4, 5, 6, 7, 8, 9, 10, 20, 30, 40, 50, or more openings) along the length of the canal. In another example, the canal includes at least one group of openings (such as at least 2, 3, 4, 5, 6, 7, 8, 9, 10, 20, 30, 40, 50, or more groups of openings) along the length of the canal. Each group of openings includes at least two openings (such as at least 3, 4, 5, 6, 7, 8, 9, 10, or more openings). In one example, the canal includes three groups of openings along the length of the canal with one group located near the first end of the canal, a second group located substantially at the middle of the canal, and a third group located near the second end of the canal.

In some examples, each opening is about 0.1-3 inches in diameter (such as about 0.5-2.5 inches, 0.5-2.0 inches, 0.5-1.5 inches, or 0.75-1.25 inches). In some examples, each opening is at least about 0.25 inches in diameter (such as at least 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0 inches). In a particular example, each opening is a hole of about 1 inch diameter. In further examples, the canal includes two or more openings or two or more groups of openings which are at least about 3 inches apart (such as at least 3, 4, 5, 6, 7, 8, 9, 10, 11, 12, 13, 14, 15, 16, 17, 18, 19, 20, 21, 22, 23, 24, or more inches apart). One of skill in the art can determine the size, spacing and number of openings in the canal for introduction of the culture to the upper end of at least one cultivation area that provides appropriate flow rate and mixing for growth of a particular organism, for example, using computational fluid dynamics (such as volume of fraction method). In one example, computational fluid dynamics are determined with a software package, such as Fluent™ (Ansys, Canonsburg, Pa.).

In additional embodiments, a disclosed system includes a return pipe that receives the culture from the pump and delivers the culture to the canal. In some examples, the return pipe is a pipe. In other examples, the return pipe is an at least partially open structure, such as a trough or canal structure. In some examples, the return pipe has an upper end and a lower end, wherein the upper end has a higher elevation than the lower end. In particular examples, the lower end of the return pipe is connected to the pump, for example by a riser pipe (such as a section of tubing or pipe) such that the pump delivers the culture from the collection area to the lower end of the return pipe. In some examples, the lower end of the return pipe is connected to a stand pipe, which is in turn connected to the pump by the riser pipe. In some examples, the upper end of the pipe is connected to the canal, such that the culture is delivered from the pipe to the canal. In other examples, the pump is directly connected to the canal (for example, in the case of a screw pump or water wheel).

In further embodiments, the bottom of at least one of the plurality of cultivation areas includes at least one flow disturbance means. The one or more flow disturbance means provide turbulence and mixing of the culture. Turbulence must be sufficiently high to mix water in the flow stream in order to expose all of the organisms in the culture (for example algae) to sunlight. Although increased turbulence in the basins will increase the exposure of the culture to sunlight; it may also be harmful to some organisms. One of skill in the art can determine the appropriate type, shape, size, and placement of flow disturbance means to provide optimal mixing and flow rates, for example, utilizing computational fluid dynamics (CFD). Light penetration depth may also be considered in the analysis. CFD can also be used to simulate chemical diffusion within the water stream and to and from the atmosphere, heat and mass transfer, and other important parameters governing culture growth.

In some examples, the flow disturbance means is a structure adjacent to (for example in direct contact with) the bottom surface of a cultivation area. The flow disturbance means can include a baffle or rib that projects upward from the bottom surface of the cultivation area (for example, at a substantially 90° angle). In some examples, the length of the flow disturbance means is oriented at an angle of about 15°-75° (such as about 20°, 30°, 40°, 45°, 50°, 60°, 70°, or 75°) relative to an axis parallel to the lower end of the cultivation area. In other examples, the length of the flow disturbance means is oriented at an angle of about 15°-75° (such as about 20°, 30°, 40°, 45°, 50°, 60°, 70°, or 75°) relative to the flow of the culture through the system. In some examples, the flow disturbance means has a length of about 10%-40% of the length of the lower end of the cultivation area (such as about 10%-30%, 20%-40%, or 15%-35% of the length of the lower end of the cultivation area). In a particular example, the length of the flow disturbance means is about 20% of the length of the lower end of the cultivation area. In further examples, the flow disturbance means is completely submerged below the water surface, when the system is in operation. In other examples, at least about 5% of the flow disturbance means projects above the water surface (such as about 10%, 15%, 20%, 25% or more of the flow disturbance means).

In some examples, the flow disturbance means is a gravel-filled tube or a section of plastic (composite) lumber. In a particular example, the flow disturbance means is a gravel-filled tube placed on the bottom surface of the cultivation area at the lower end of the cultivation area at a 45° angle relative to an axis parallel to the lower end of the cultivation area. In a particular example, the flow disturbance means is about 3 feet long, with a diameter of about 6 inches. In another particular example, about 10% of the flow disturbance means projects above the water surface. In another example, the flow disturbance means includes pressurized water, for example jets of water introduced into the cultivation area.

In some embodiments of a system, the upper end of the first cultivation area and the second cultivation area are adjacent. In such an arrangement, the lower end of the first cultivation area and the second area are also adjacent and the sides of each cultivation area are substantially parallel to one another. In one example, the canal is parallel to the upper end of each of the cultivation areas in the system, and culture exits from the canal into each of the cultivation areas substantially simultaneously. In some examples, the system includes at least one intervening cultivation area (such as at least 2, 3, 4, 5, 6, 7, 8, 9, 10, 20, 30, 40, 50, or more cultivation areas) between the first and second cultivation areas. In other examples, the system includes at least 1-100 intervening cultivation areas (such as 5-100, 10-80, 10-50, 20-90, 30-80, 25-75, or 30-60). In one example, the system includes 50 intervening cultivation areas between the first and second cultivation areas. In another example, the system includes 10 intervening cultivation areas between the first and the second cultivation areas.

In other embodiments, the lower end of the first cultivation area is substantially parallel to and has a higher bottom surface elevation than the upper end of the second cultivation area. In one example, the canal is parallel to the upper end of the first cultivation area and culture exits from the canal into the first culture area. The culture then flows from the first cultivation area into the second cultivation area. In some examples, the lower end of the first cultivation area is formed by the same structure (such as a barrier, discussed below) that forms the upper end of the second cultivation area. In some examples, the system includes at least one intervening cultivation area (such as at least 2, 3, 4, 5, 6, 7, 8, 9, 10, 20, 30, 40, 50, or more cultivation areas) between the first and second cultivation areas. In other examples, the system includes at least 1-100 intervening cultivation areas (such as 5-100, 10-80, 10-50, 20-90, 30-80, 25-75, or 30-60). In one example, the system includes 10 intervening cultivation areas between the first and the second cultivation areas. In another example, the system includes one intervening culture area between the first and the second cultivation areas.

In some examples wherein the lower end of the first cultivation area is parallel to the upper end of the second cultivation area, the first and second cultivation areas (and any intervening cultivation areas) are separated by a barrier between the lower end of the first cultivation area and the upper end of the second cultivation area that is substantially parallel to the lower end of the cultivation area. The barrier extends from one side of the cultivation area to the other side of the cultivation area. In some examples, the barrier includes a structure having a round cross section, for example a pipe or tube. In other examples, the barrier includes a structure having a square or rectangular cross-section. In one example, the barrier is a flexible tube (for example, a plastic tube that is filled with water). In a particular example, the barrier has a diameter of about 5-25 cm (such as about 5-20 cm, 10-20 cm, 5-15 cm, 5-10 cm). In one example, the barrier has a diameter of about 15 cm. One of skill in the art can determine appropriate size and shape for the barriers.

In a particular example, if the barrier is a flexible water-filled tube, the barrier is maintained in position by one or more backstops (such as one or more gravel-filled tubes) that prevent the barrier from shifting due to the flow of culture through the system.

The barrier is higher than the water surface elevation of the upper end of the second cultivation area when the system is in use, and produces a drop from the first cultivation area to the second cultivation area. The drop induces flow velocity in the second cultivation area and also produces turbulence in the culture. In some examples, the drop is about 1 cm to about 6 cm (such as about 1-5 cm, about 2-5 cm, about 2-4 cm, about 3-5 cm or about 4-6 cm). In some examples, the drop is at least about 1 cm, 1.5 cm, 2 cm, 2.5 cm, 3 cm, 3.5 cm, 4 cm, 4.5 cm, 5 cm, 5.5 cm, or 6 cm. In one example, the drop is about 3 cm. In some examples, the system includes intervening cultivation areas between the first and second cultivation areas, and each cultivation area is separated from the next by a barrier, creating a drop as described above.

The barrier between each of the cultivation areas includes at least one flow pathway that permits flow of the culture from one cultivation area to the next cultivation area. In some examples, the flow pathway includes at least one opening in the barrier. In some examples, the barrier includes multiple openings or groups of openings along the length of the barrier, allowing flow of the culture from the lower end of one cultivation area to the upper end of the next cultivation area. In a particular example, the barrier includes at least two openings (such as at least 3, 4, 5, 6, 7, 8, 9, 10, 20, 30, 40, 50, or more openings) along the length of the barrier. In another example, the barrier includes at least one group of openings (such as at least 2, 3, 4, 5, 6, 7, 8, 9, 10, 20, 30, 40, 50, or more groups of openings) along the length of the barrier. Each group of openings includes at least two openings (such as at least 3, 4, 5, 6, 7, 8, 9, 10, or more openings). In one example, the barrier includes three openings along the length of the barrier with one opening located near a first end of the barrier, a second group located substantially at the middle of the length of the barrier, and a third group located near a second end of the barrier.

In other examples the flow pathway includes at least one depression in the top of the barrier that places the top of the barrier below the water surface of the culture for at least a portion of the length of the barrier. In some examples, the barrier includes two or more depressions, such as 2, 3, 4, 5, or more depressions. In some examples, the length of the depression is about 0.5-20% of the length of the barrier (such as about 1-20%, 1-15%, 1-5%, 2-20%, 2-10%, or 2-5%). In other examples, the length of the depression is at least about 0.5% (for example, at least about 0.6%, 0.7%, 0.8%, 0.9%, 1.0%, 1.1%, 1.2%, 1.3%, 1.4%, 1.5%, or more) of the length of the barrier. In a particular example, the length of the depression is about 0.5% or about 1% of the length of the barrier. In other examples, the length of the depression is at least about 1 inch, such as about 1, 1.5, 2, 2.5, 3, 2.5, 4, or 5 inches.

In a particular example, the barrier is a flexible tube, and a depression is produced by placing a weight (such as a sandbag) on the top of the barrier. In other examples, the flow pathway includes a gap between the bottom surface of the cultivation area and the bottom of the barrier. In a particular example, the barrier is a flexible tube, and a gap is produced by placing an object between the bottom of the tube and the bottom surface of the cultivation area, raising the barrier and creating a gap. For example, a small piece of pipe, such as pipe having a diameter of about 0.25-2 inches (such as about 0.25-1.5 inches, 0.5-2 inches, 0.5-1.5 inches, or 0.25-1 inch) can be placed under the barrier, creating a flow pathway. One of skill in the art can identify additional objects that can be used to depress the barrier or raise the barrier to create one or more flow pathways.

In some embodiments, the system also includes a barrier (such as a barrier described above) including at least one flow pathway between the lower end of at least one cultivation area and the collection area. In other embodiments, the barrier between the cultivation areas and/or between the lower end of at least one cultivation area and the collection area includes a weir. The weir can be automated or manual. In some examples the weir is constructed with boards or blocks and the height of the weir can be adjusted by adding or removing one or more boards or blocks.

In some embodiments, a disclosed system includes a cover for at least a portion of at least one of the plurality of cultivation areas, the collection area, the canal, or a combination of two or more thereof. In some examples, the cover is placed over at least a portion of at least one cultivation area, at least a portion of the collection area or at least a portion of the canal. The cover does not completely isolate the system (or a portion of the system) from the environment. In some examples, the cover can help regulate the water temperature in the system by reducing radiation and sensible heat loss from the water (such as from the collection area, for example during nighttime hours). In additional examples, the cover can help regulate water temperature by blocking solar radiation to reduce heating of the water (for example, during hot and dry months). The cover can also help reduce water loss by evaporation (for example during hot and dry months). In some examples, the system includes a cover over the collection area (such as during times when the culture is stored in the collection area, for example, during night time hours). In other examples, the system includes a cover over one or more of the cultivation areas (such as during hot and dry months, such as summer months).

In particular non-limiting examples, the cover includes a greenhouse cover (such as a greenhouse hoop structure), a swimming pool cover, a shading net (such as used in greenhouse or nursery operations), a tarpaulin (such as a plastic or cloth tarpaulin), Mylar®, or a combination thereof (for example, different portions of the system may be covered with different types of covers). Examples of cover materials include glass, plastic (for example, polyvinyl chloride, polypropylene, polyethylene, or acrylic), or fabric (such as polyester). In some examples, the cover allows transmission of photosynthetic active radiation, while reflecting near infrared radiation. In a particular example, the cover is retractable (e.g., roll-A-roof®) and can be operated manually or automatically.

In some embodiments of the system, one or more sensors are optionally included. In some examples, sensors and instrumentation are included to monitor one or more parameters of the algae culture, the environment, or both. Culture parameters that may be monitored include water temperature, electrical conductivity, pH, carbon dioxide, dissolved oxygen, optical density (e.g., algal density), ion concentration (e.g., calcium concentration) and water flow speed. Environmental parameters that may be monitored include air temperature, relative humidity, solar radiation, photosynthetic active radiation, and wind speed. The sensors for measuring culture parameters are placed in one or more location in the system, for example, at least one sensor is placed in the collection area, canal, at least one of the plurality of cultivation areas, or a combination of two or more thereof. In some examples, sensors for a particular parameter are placed in more than one location in the system. In a particular example, sensors for optical density of the culture are placed in the canal, at least one cultivation area, and the collection area. One of skill in the art can select appropriate numbers and locations for sensors for any particular parameter. One or more sensors for monitoring environmental parameters are placed in close proximity to the culture system, such as within at least 2 kilometers of the system (for example, within at least about 1.5 kilometers, 1 kilometer, 500 meters, 100 meters, or 50 meters of the canal or the collection area).

A data acquisition system (e.g., a data logger and wireless connection hub) can be used to connect one or more sensors and to monitor and record collected data. In some embodiments, the data acquisition system is connected to a remote access system for observation of the culture status and environment. In one example, an integrated process control system is utilized for the distributed control of the aquaculture system. The distributed control system (DCS) is composed of multiple sensors/transducers that convert culture and environmental conditions into electrical signals, communication multiplexers that convert the sensor's electrical signals into digital code, computer hardware that can receive the transmitted signals from and to the multiplexers, computer hardware that interfaces to a human user, and computer software configured to provide a graphical interface for representing trending incoming data and trending historical data. In some examples, high level integration of the data and system parameters is managed by artificial intelligence computer programs (e.g., rule-based expert system, neural nets, fuzzy-logic-based expert systems, and neural fuzzy systems). Based on data collection and analysis, one of skill in the art can estimate growth rate and carbon dioxide and nutrient requirements of a culture. Such analysis can also enable one of skill in the art to optimize nutrient injection points, exposure time, and duration between injections.

II. Description of Particular Embodiments

FIG. 1 is a top view of an embodiment of the disclosed aquaculture system 100. The system 100 includes a plurality of cultivation areas 102, each of which includes a substantially parallel upper end 104 and lower end 106, with the upper end having a higher bottom surface elevation than the lower end. Each cultivation area also includes a bottom surface 108. The plurality of cultivation areas are situated such that the lower end of a first cultivation area 102a is adjacent to and substantially parallel with the upper end of a second cultivation area 102b and the lower end of the second cultivation area 102b is adjacent to and substantially parallel to the upper end of a third cultivation area 102c. The first cultivation area 102a has a higher bottom surface elevation than the second cultivation area 102b, and the second cultivation area 102b has a higher bottom surface elevation than the third cultivation area 102c. Each of the cultivation areas is separated by a barrier 110. Each cultivation area also includes baffles 112 that provide flow disturbance when culture is flowing through the system. Flow direction through the system is shown by arrows.

The system 100 also includes a collection area 114 that is located below the lower end 106 of the third cultivation area 102c. The bottom surface elevation of the third cultivation area 102c is higher than that of the collection area 114. The collection area 114 has a bottom surface 116 and two sloped sides 118. The collection area 114 includes at least one air line 120 for introducing gases into the culture. The collection area 114 also includes a pump 122 which returns the culture from the collection area 114 to the upper end 104 of the first cultivation area 102a. The culture is carried from the pump 122 through a riser pipe 124 to a return pipe 126. The return pipe is connected to a canal 128 that has a higher elevation than the first cultivation area 102a.

Figure 2:
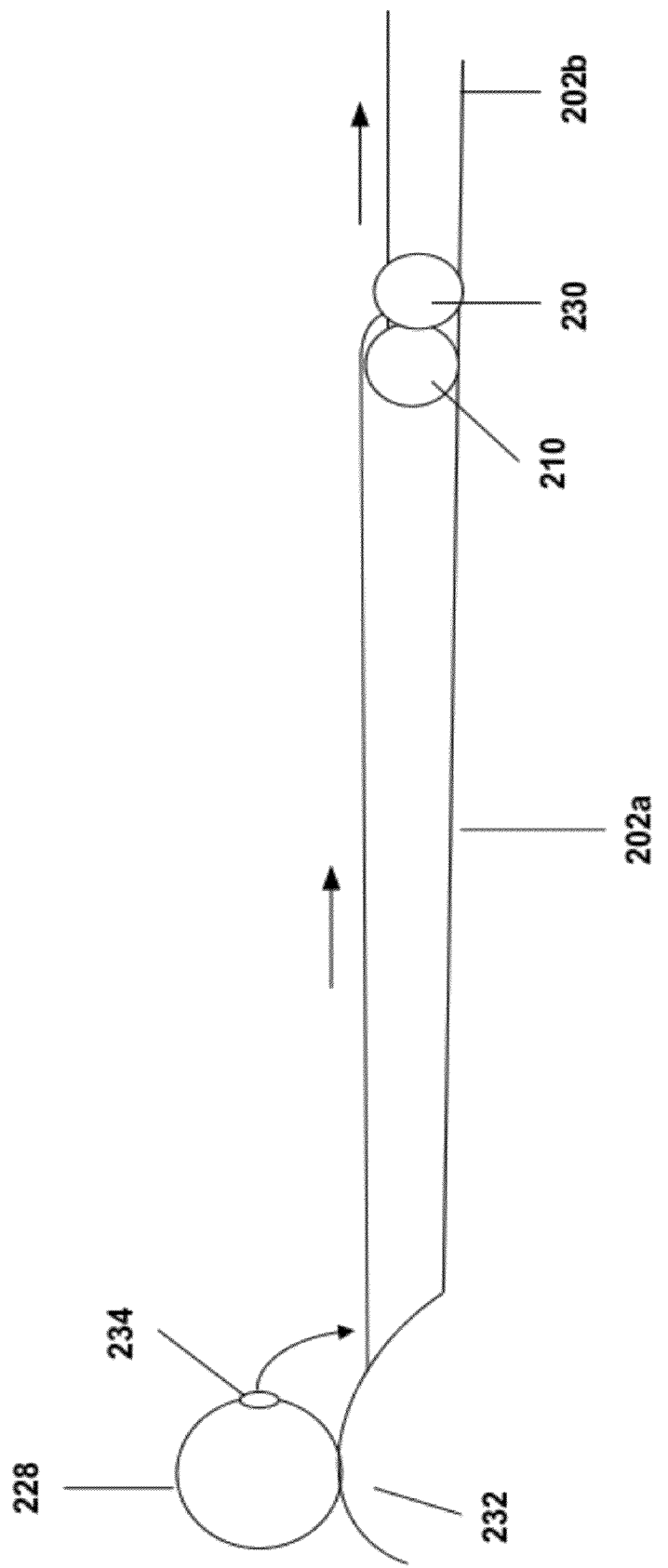
FIG. 2 is a side view of the upper portion of the system shown in FIG. 1.

FIG. 2 shows a side view of the canal 228 and first cultivation area 202a and second cultivation area 202b. The cultivation areas are separated by a barrier 210, which is held in place by a backstop 230. The canal 228 rests on an earthen berm 232, providing a higher water surface elevation than the first cultivation area 202a. The canal 228 has at least one opening 234 from which culture flows during circulation in the system. The flow direction of culture through the system is shown by arrows.

Figure 3:
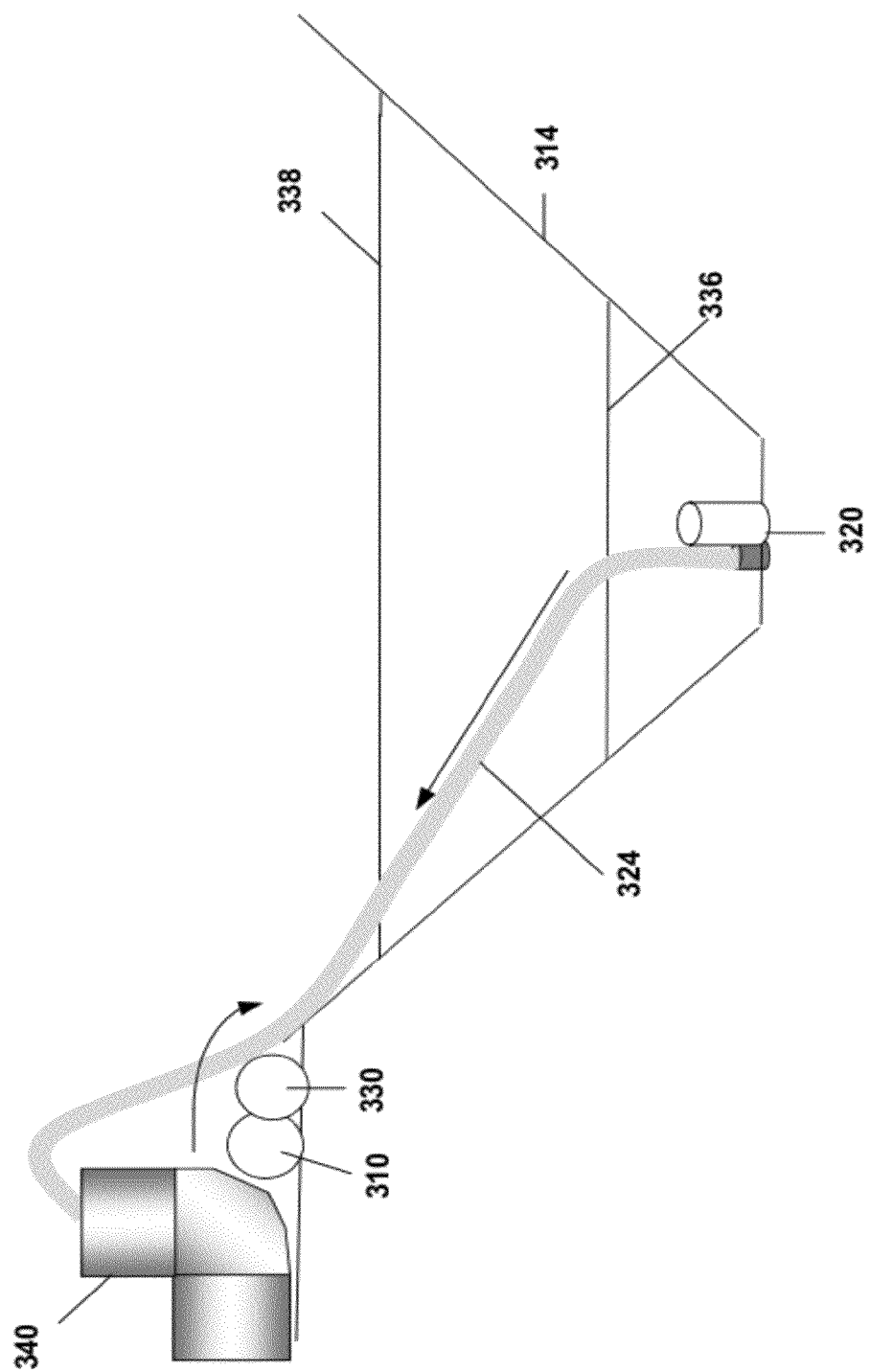
FIG. 3 is a side view of the collection area shown in FIG. 1.

FIG. 3 is a side view of the collection area 314 showing the return of culture from the collection area to the return pipe (not shown). The depth of the culture during circulation 336 is less than the depth of the culture during storage 338. The collection area 314 includes a pump 320 that lifts the culture through a riser pipe 324 to a stand pipe 340. In some examples, the stand pipe 340 is adjacent to the barrier 310 and backstop 330. The direction of flow of culture through the system is shown by arrows.

Figure 4:
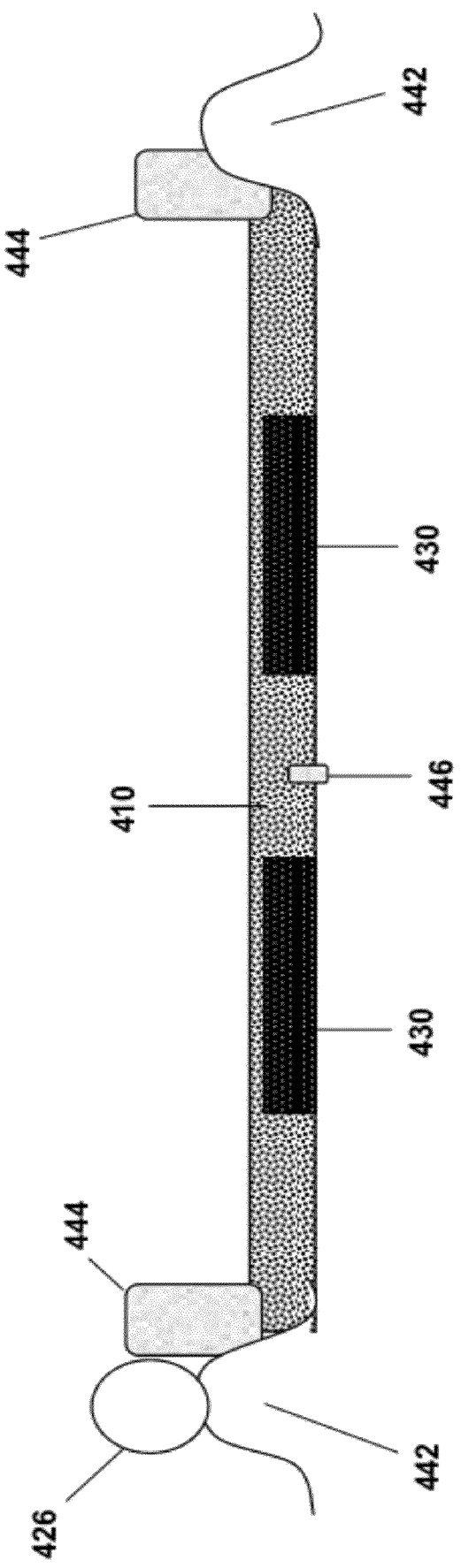
FIG. 4 is a plan view of a cultivation area shown in FIG. 1.

FIG. 4 is a plan view of a cultivation area from a perspective substantially parallel to the barrier 410. The sides of the cultivation area are formed by an earthen berm 442. The return pipe 426 rests on the earthen berm 442 on one side of the cultivation area. The barrier 410 is held in place by two backstops 430. The barrier 410 is also secured at each end by a sandbag 444 or other weight that also depresses the flexible barrier 410, creating a flow pathway for the culture. The flexible barrier 410 is also raised by the insertion of a small object 446, which creates an additional flow pathway for the culture.

Figure 5:
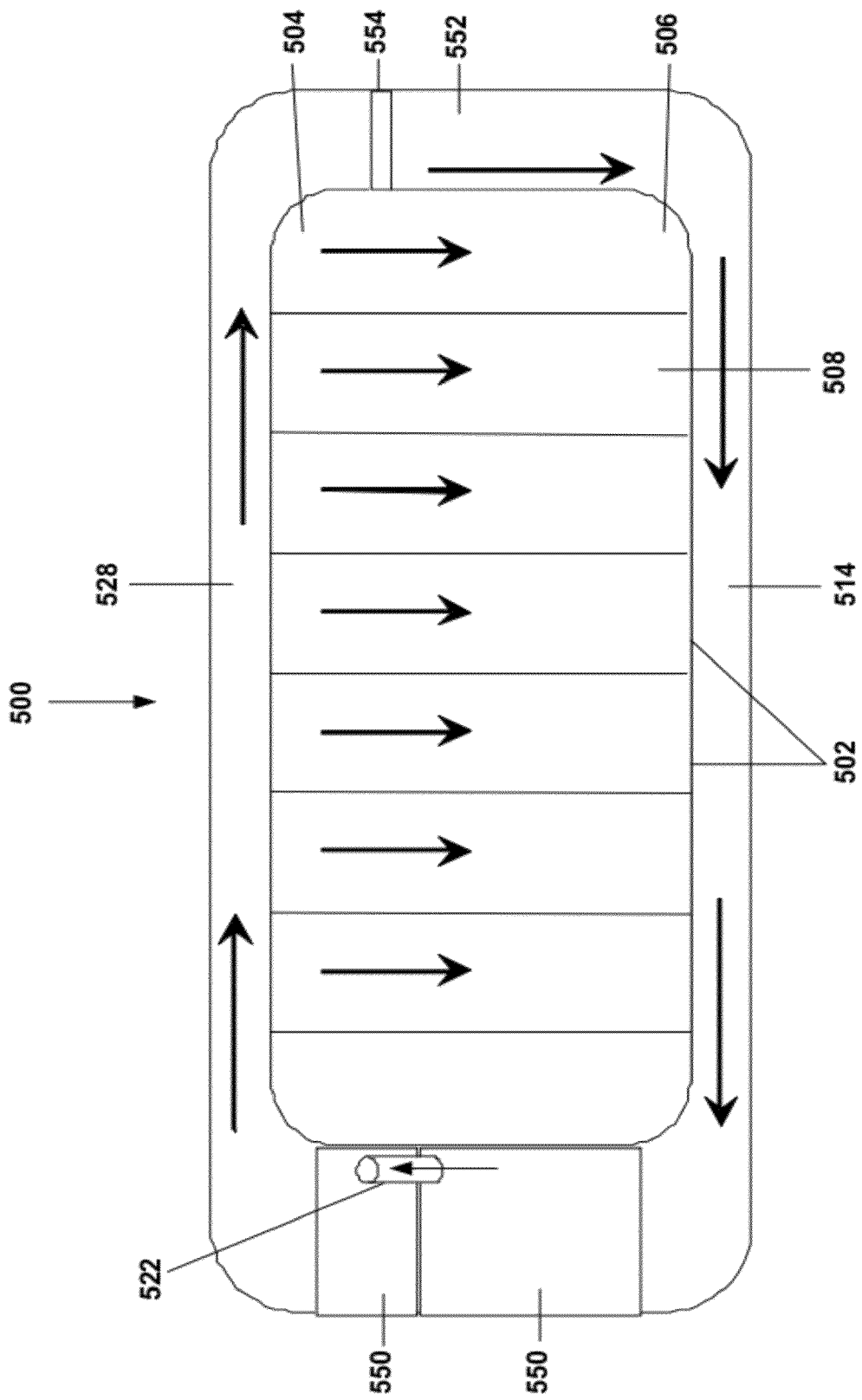
FIG. 5 is a top view of an exemplary alternative embodiment of a system for aquaculture disclosed herein.

FIG. 5 is a top view of an alternative embodiment of the disclosed aquaculture system 500. The system 500 includes a plurality of cultivation areas 502, each of which includes a substantially parallel upper end 504 and lower end 506, with the upper end having a higher bottom surface elevation than the lower end. Each cultivation area also includes a bottom surface 508. In this embodiment, the upper ends 504 of each cultivation area 502 are adjacent to one another. The system also includes a collection area 514 that is located below the lower ends 506 of the cultivation areas 502. The bottom surface elevation of the cultivation areas 502 is higher than that of the collection area 514. The collection area 514 includes areas that can be used for algae settling, flotation, and/or harvesting 550. The collection area 514 also includes a pump 522 which returns the culture from the collection area 514 to a canal 528 that is substantially parallel to the upper ends 504 of the cultivation areas 502. The canal 528 that has a higher bottom surface elevation than the cultivation areas 502. This embodiment also includes a channel 552 that connects the canal 528 and the collection area 514, wherein the channel 552 is parallel to the cultivation areas 502. The flow through the channel is regulated by a weir 554. Arrows show the flow direction of culture through the system.

III. Methods of Regulating Culture Temperature Using the ARID System

Disclosed herein are methods of regulating culture temperature utilizing embodiments of the ARID culture system described above. The method maximizes surface area exposure of the culture to solar radiation during the daytime and minimizes long wave radiation to the sky and heat transfer to the atmosphere at night during winter months in order to maintain water temperature above a minimum threshold temperature. Conversely, the method minimizes surface area exposed to direct solar radiation during the day and maximizes long wave radiation to the sky and heat transfer to the atmosphere at night during the summer months in order to maintain water temperature below a maximum threshold temperature. In additional examples, if the soil is cooled at night, then the soil in the cultivation areas acts to cool the water during the day as it flows through the cultivation areas.

The disclosed method includes circulating a culture (such as an algae culture) through the culture system described herein and storing the culture in an area of the system (for example, storing the culture in at least one cultivation area or the collection area) for at least a portion of a 24 hour period, thereby regulating the water temperature of the culture. In some examples, the method includes circulating the culture through the system described herein, and storing the culture in the collection area for at least a portion of a 24 hour period. In other examples, the method includes circulating the culture through the system described herein, and storing the culture in at least one of the cultivation areas for at least a portion of a 24 hour period. In further examples, the method includes circulating the culture through the system described herein, and storing the culture in the collection area and at least one cultivation area for a portion of a 24 hour period.

In some embodiments, the method includes circulating the culture through the system (for example in a loop through the cultivation areas and the collection area) in the presence of solar radiation to increase the water temperature. When the culture is circulating through the system in the presence of solar radiation, the surface area of the culture is maximized (distributed over the plurality of cultivation areas and the collection area), thereby increasing absorption of solar radiation and increasing the water temperature. In other embodiments, the method includes circulating the culture through the system (for example in a loop through the cultivation areas and the collection area) during a period of lower relative solar radiation to decrease the water temperature. In some examples, a period of lower relative solar radiation includes a period substantially lacking solar radiation, for example, at night or during periods of substantially complete cloud cover). In other examples, a period of lower relative solar radiation includes a period with decreased solar radiation from peak sunlight hours (for example, early morning or early evening hours or periods of partial cloud cover). In a particular example, peak sunlight hours (a period of higher relative solar radiation) is between 9:00 a.m. and 4:00 p.m. in winter (e.g., November to January) and between 7:00 a.m. and 7:00 p.m. in summer (e.g., May to July) in Tucson, Ariz. One of skill in the art can determine periods of higher and lower relative solar radiation, for example, based on latitude and season. When the culture is circulating through the system during periods of lower relative solar radiation, the surface area of the culture is maximized (distributed over the plurality of cultivation areas and the collection area), thereby increasing long wave radiation and heat transfer to the environment, and decreasing the water temperature.

In some embodiments, the method includes storing the culture in the collection area for at least a portion of a 24 hour period to maintain the water temperature at or above a minimum temperature (for example, about 15° C. to about 20° C., such as about 15° C., 16° C., 17° C., 18° C., 19° C., or 20° C.). Storing the culture in the collection area decreases the surface area of the culture, decreasing long wave radiation to the sky and heat transfer to the atmosphere, thereby reducing any decrease in water temperature and maintaining the water temperature at or above the minimum temperature. In some examples, the culture is stored in the collection area during periods of lower relative solar radiation, such as night time hours and/or in the presence of cloud cover or during early morning or late evening hours. In particular examples, the culture is stored in the collection area during night time hours during the winter months. In other examples, the culture is stored in the collection area during only a portion (less than all) of the night time hours (such as at least about 0.5, 1, 2, 3, 4, 5, 6, 7, 8, 9, 10, or more hours) during the summer months, when less heat transfer to the atmosphere occurs. In additional examples, the culture is stored in the collection area during a portion of day time hours (for example, at least about 0.5, 1, 2, 3, 4, 5, 6, 7, 8, 9, 10 or more hours), to reduce solar radiation and water temperature. In some examples, the culture is stored in the collection area during a portion of the day time hours during warm, humid times of the year (for example, at least about 0.5, 1, 2, 3, 4, 5, 6, 7, 8, 9, 10 or more hours). One of skill in the art can determine the length of time the culture is stored based on environmental conditions (for example, amount of solar radiation), culture temperature, and desired temperature range of the culture.

In other embodiments, the method includes storing the culture in one or more of the cultivation areas for at least a portion of a 24 hour period to maintain the water temperature at or below a maximum temperature (for example, about 30° C. to about 35° C., such as about 30° C., 31° C., 32° C., 33° C., 34° C., or 35° C.). Storing the culture in one or more cultivation areas increases the surface area of the culture, increasing long wave radiation to the sky and heat transfer to the atmosphere, thereby decreasing the water temperature and maintaining the water temperature at or below the maximum temperature. In some examples, the culture is stored in one or more cultivation areas during periods of lower relative solar radiation, such as night time hours and/or in the presence of cloud cover or during early morning or late evening hours. In particular examples, the culture is stored in one or more cultivation areas during night time hours during the summer months. In other examples, the culture is stored in one or more cultivation areas during only a portion (less than all) of the night time hours (such as at least about 0.5, 1, 2, 3, 4, 5, 6, 7, 8, 9, 10, or more hours). In further examples, the culture is stored in one or more cultivation areas during one or more portions of day time hours to increase water temperature (such as at least about 0.5, 1, 2, 3, 4, 5, 6, 7, 8, 9, 10 or more hours). One of skill in the art can determine the length of time the culture is stored based on environmental conditions, culture temperature, and desired temperature range of the culture.

In further embodiments, the method includes providing an additional (e.g., non-solar) temperature regulation device in order to maintain the water temperature at or above a minimum temperature (such as above about 15° C., 16° C., 17° C., 18° C., 19° C., or 20° C.) or to maintain the water temperature at or below a maximum temperature (such as below about 30° C., 31° C., 32° C., 33° C., 34° C., or 35° C.). In some examples, the method includes increasing the water temperature by the temperature regulation device included in the system (described above). In a particular example, additional heat is provided during the winter months, particularly during early morning hours. In other examples, the method includes decreasing the water temperature by the temperature regulation device included in the system. In a particular example, cooling is provided during the summer months, particularly during hours of intense solar radiation (for example in the middle of the day).

In particular embodiments, the method described herein can be used to maintain the water temperature in the system at about 15° C. to 35° C. (such as about 15, 16, 17, 18, 19, 20, 21, 22, 23, 24, 25, 26, 27, 28, 29, 30, 31, 32, 33, 34, or 35° C.). One of skill in the art can select the appropriate temperature or temperature range, based on the organism being cultured in the system. In some examples (such as algae cultivation, for example *Botryococcus braunii*), the temperature is maintained at about 20° C. to about 30° C. (such as about 20° C. to 28° C.).

The method includes circulating the culture through the culture system disclosed herein. Circulation increases the surface area of the culture exposed to solar radiation, promoting photosynthesis, respiration, and growth of the culture organisms. Circulation also provides mixing (in some examples, in combination with flow disturbance means included in the system), increasing exposure to solar radiation, carbon dioxide, and nutrients. In particular examples, the flow rate of the culture circulating through the system is about 0.1 m/min to about 2.5 m/min (such as about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, or 2.5 m/min). In one example, the flow rate is about 0.3 m/min. One of skill in the art can select an appropriate flow rate based on the organism being cultured and the configuration of the system (for example, utilizing computational fluid dynamics).

The depth of the culture in the cultivation areas and collection area during circulation depends on the configuration of the system (for example, the number and dimensions of the cultivation areas or the dimensions of the collection area), the volume of the culture, and the flow rate. In some examples, the average depth of the culture in the cultivation areas during circulation is about 10-75 cm (such as about 10-70 cm, 10-60 cm, 10-50 cm, 20-60 cm, 20-50 cm, 30-75 cm, 30-60 cm, 10-20 cm, or 5-15 cm). In a particular example, the average depth of the culture in the cultivation areas during circulation is about 12 cm. In some examples, the average depth of the culture in the collection area during circulation is about 10-75 cm (such as about 10-70 cm, 10-60 cm, 10-50 cm, 20-60 cm, 20-50 cm, 30-75 cm, 30-60 cm, or 40-60 cm). In a particular example, the average depth of the culture in the collection area during circulation is about 50 cm. One of skill in the art can select an appropriate average depth of culture in the cultivation areas and collection area during circulation based on the organism being cultured and the configuration of the system (for example, utilizing computational fluid dynamics).

The depth of the culture in the cultivation areas and/or collection area during storage depends on the configuration of the system (for example, the number and dimensions of the cultivation areas or the dimensions of the collection area) and the volume of culture in the system. In some examples, the average depth of the culture during storage in the collection area is about 75 cm to about 200 cm (such as about 100-200 cm, 100-175 cm, 100-150 cm, 75-175 cm, 75-150 cm, or 125-175 cm). In a particular example, the average depth of culture in the collection area during storage is about 150 cm. In further examples, the average depth of the culture during storage in the cultivation areas is about 1-50 cm (such as about 5-40 cm, 5-30 cm, 5-25 cm, 10-30 cm, 10-25 cm, or 10-20 cm). In a particular example, the average depth of the culture in the cultivation areas during storage is about 10 cm. In some examples, the culture is stored in both the cultivation areas and the collection area simultaneously (for example, a portion of the culture is stored in the collection area and a portion of the culture is stored in at least one cultivation area).

In additional examples, the method includes harvesting the culture (for example, harvesting algae from an algae culture). Methods for algae harvesting are well known to one of skill in the art. In some examples, a portion of the culture is retained in the system (for example, in the return pipe) for use as inoculum for continued culture production. In some examples, the culture stored for inoculum use is about 1000-10,000 liters (such as about 1000-7500 liters, 2000-10,000 liters, 3000-5000 liters, or about 4000 liters). In other examples, a proportion of the culture is retained for inoculation of the new culture, for example about 10-50% of the total harvested culture volume (such as about 10-40%, 10-35%, 20-50%, 20-40%, 30-35%, or about 33% or the total harvested culture volume). The volume or percentage of the culture needed for use as inoculum can be determined by one of skill in the art, for example, based on the density of the culture at harvesting and the total volume of water that will be inoculated.

In some embodiments, the method includes covering at least a portion of the system (for example, the collection area or at least one of the cultivation areas) during a portion of a 24 hour period. The covers that can be used are discussed above, and are well known to one of skill in the art. In some examples, the method includes covering the collection area and/or the cultivation areas during storage of the culture. In one example, the collection area is covered during storage of the culture during periods of lower relative solar radiation (such as at night or during a period of cloud cover) in order to further reduce long wave radiation to the sky and heat transfer to the atmosphere, thereby maintaining the water temperature at or above a minimum temperature (such as about 15° C.-20° C.). In another example, the collection area and/or the cultivation areas are covered during storage of the culture during periods of higher relative solar radiation (such as day time hours, for example peak sunlight hours) to reduce solar radiation reaching the water surface and heat transfer from the atmosphere, thereby maintaining the water temperature at or below a maximum temperature (such as 30° C.-35° C.).

In other examples, the method includes covering the cultivation areas and/or the collection area during circulation of the culture. In one example, the cultivation areas are covered during circulation to reduce long wave radiation to the sky and heat transfer to the atmosphere, thereby maintaining the water temperature at or above a minimum temperature (such as about 15° C.-20° C.). In another example, the collection area and/or the cultivation areas are covered during circulation of the culture to reduce solar radiation reaching the water surface and heat transfer from the atmosphere, thereby maintaining the water temperature at or below a maximum temperature (such as 30° C.-35° C.).

In further embodiments, the method includes use of the reflective and absorptive properties of the liner used for the bottom surface of the cultivation areas and/or the collection area to further regulate the water temperature of the culture. In some examples, the liner is a dark color that absorbs solar radiation (for example, black). In other examples, the liner is a light color that reflects solar radiation (for example, white). In particular examples, an absorptive (e.g., black) liner is used in the winter season or in temperate climates with cooler daytime temperatures, in order to maximize heat absorption by the system and maintain the culture at or above a desired minimum temperature. In other particular examples, a reflective (e.g., white) liner is used in the summer season or in arid climates with warmer daytime temperatures, in order to minimize heat absorption by the system and maintain the culture at or below a desired maximum temperature. In a particular example, a reflective (e.g., white) liner is placed over the absorptive (e.g., black) liner during the summer season, rather than replacing the liner entirely.

In other examples, a radiant barrier is created by placing a reflective material (such as foil or MYLAR®) between the liner and the soil. In some examples, an air gap is created between the liner and the reflective material by injecting air (for example, from a pneumatic device) below the liner when the cultivation area is drained of water and/or culture. In this case, the water is in direct thermal contact with the soil when the cultivation area is filled with water, but there is a thermal barrier (air gap and no radiation) between the soil and atmosphere when the cultivation area is drained of water and/or culture. This can prevent the soil from losing energy at night and/or taking energy out of the water when the cultivation areas are refilled.

The methods disclosed herein are suitable for culturing a wide variety of species, including, but not limited to microalgae. In some examples, the algae species include, but are not limited to *Chlorella, Chlamydomonas, Chaetoceros, Spirulina, Dunaliella*, and *Porphyridum*. In particular examples, the algae species include algae useful for production of biofuels, such as *Akistrodesmus, Botryococcus braunii, Chlorella* (such as *Chlorella* sp. or *Chlorella prototothecoides*), *Crypthecodinium cohnii, Cyclotella, Dunaliella tertiolecta, Gracilaria, Hantzschia, Nannochloris, Nannochloropsis, Neochloris oleoabundans, Nitzschia, Phaeodactylum tricornutum, Pleurochrysis carterae* (also called CCMP647), *Sargassum, Scenedesmus, Schiochytrium, Stichococcus, Tetraselmis suecica*, and *Thalassiosira pseudonana*. In one example, the algae species is *Botryococcus braunii*.

EXAMPLES

Example 1

Comparison of ARID System and Conventional Open Raceway Temperatures

This example describes simulations comparing water temperature in a disclosed ARID system and a conventional open raceway design.

Figure 6:
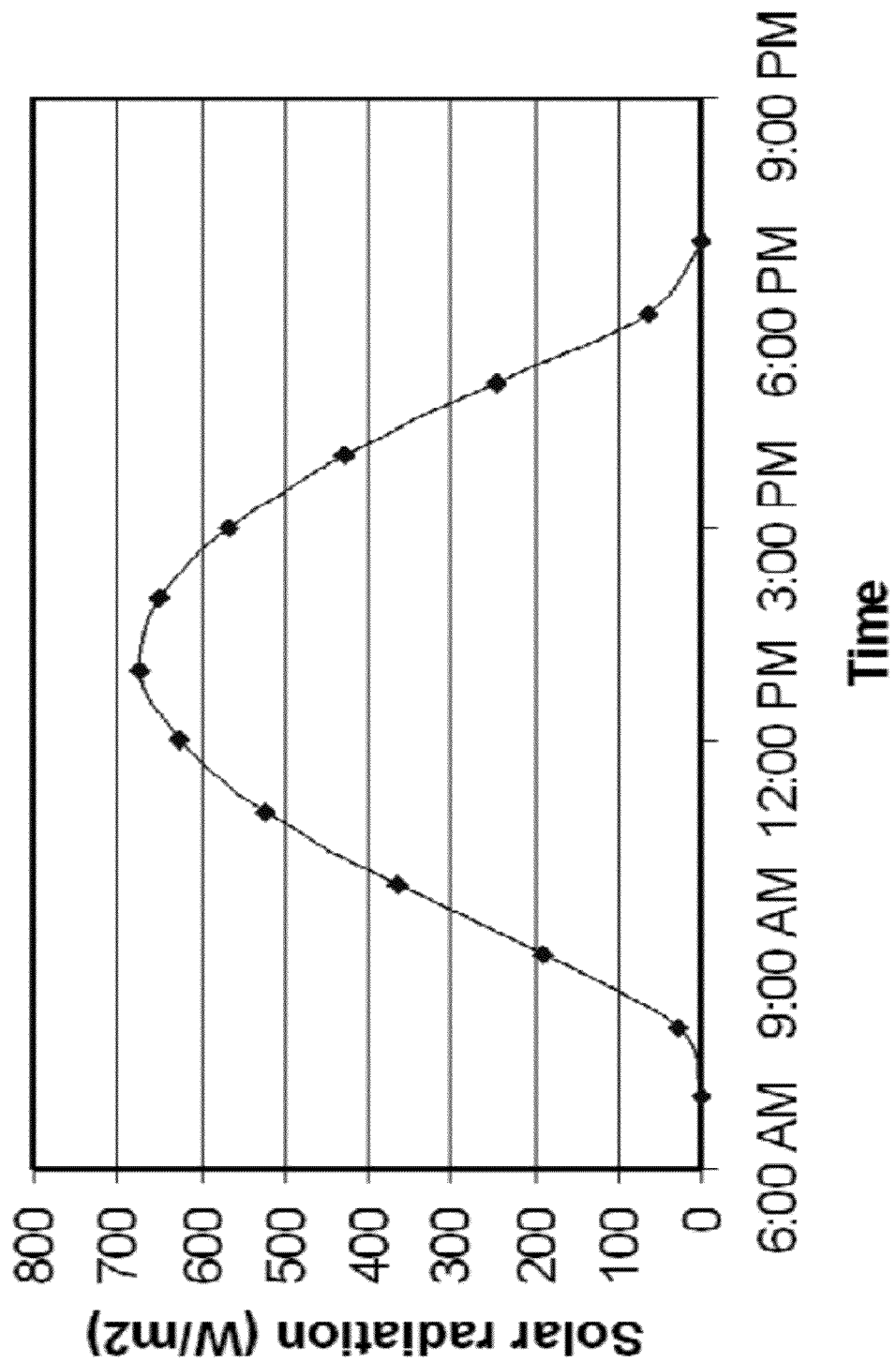
FIG. 6 is a graph showing typical solar radiation intensity during January in Tucson, Ariz.

Tucson, Ariz. has high solar radiation intensity and 360 sunny days per year. Winter solar radiation intensity, a limiting factor in algae production is relatively high with a maximum unit power of nearly 700 W/m$^2$ at midday (FIG. 6). The limitation on algae production in the Southern Arizona desert in winter is that open pond temperatures drop below the acceptable range (e.g., below 20° C. to 28° C.), based on the experience of algae researchers at the University of Arizona. The simulations were conducted with Arizona Meteorological Network (AZMET) hourly data from January, 2009. AZMET data includes solar radiation, reference evapotranspiration, and the assumption that basins (cultivation areas) are drained into raceways (collection area) at 5 p.m. and filled at 8 a.m. It was also assumed that the collection area was covered at night with a clear plastic cover that reduced radiation and sensible heat loss by 83%. The percent of solar radiation that entered the water during the day was 80% (20% was reflected). Evaporation was 90% of AZMET calculated evapotranspiration. The ARID design used in these simulations is that shown in FIG. 5, with the parameters shown in Table 1. It was also assumed that there was no net heat loss from cultivation area soils at night. This implies that a radiant barrier or insulating board is placed under the liner.

TABLE 1

Canal and basin parameters

| Parameter | Dimension |
|---|---|
| Basin width | 5.8 m |
| Number of basins | 52 |
| Basin length | 30 m |
| Basin flow velocity | 0.01 m/sec |
| Basin retention time | 50 min |
| Average basin depth | 15 cm |
| Basin flow rate | 0.0087 m³/sec |
| Total system flow in basins | 0.45 m³/sec |
| Basin volume | 26.1 m³ |
| Raceway length | 300 m |
| Trapezoidal canal dimensions | |
| Bottom width | 1.35 m |
| Side slope z | 2 |
| Depth | 0.8 m |
| Perimeter | 4.927708764 m |
| Area | 2.36 m² |
| Hydraulic radius | 0.478924407 m |
| Top width | 4.55 m |
| Volume in each canal | 708 m³ |
| Mannings n | 0.02 |

The thermal energy balance was based on the sensible heat flux, net long wave radiation, evaporation and associated latent heat of vaporization, and solar radiation. The sensible heat flux (natural convection heat transfer) is related to the temperature difference between the water surface and the air. It can be calculated based on atmospheric boundary layer equations (Oke, *Boundary Layer Climates*, Routledge, Inc., 1987). It is assumed that the water is well mixed and that the water surface temperature is approximately homogenous in cultivation areas or canals.

$$Q_H = \frac{C_a(T_a - T_0)}{r_{aH}}$$

where $$C_a = rc_p$$
$$= (1.1 \text{ kg}/m^3)(1010 \, J \, kg^{-1}K^{-1})$$
$$= 1,111 \, J \, m^{-3}K^{-1}$$
$$= 1.11 \, kJ \, m^{-3}K^{-1}$$

$Q_H$=sensible heat transfer (+inward), kJ m$^{-2}$
$T_a$=bulk air temperature, C
$T_0$=water or soil surface temperature.

The resistance to sensible heat transfer can be calculated as a function of wind speed.
The following general equation assumes neutral air stability.

$$r_{aH} = \frac{\left[\ln\frac{z_2}{z_1}\right]^2}{k^2\Delta u}$$

where
  $z_1$=roughness height, assumed to be 1/10 of change in surface elevation.
  $z_2$=elevation of wind speed measurement, 3 m AZMET station elevation.
  K=von Karman's constant, 0.4,
  $r_{aH}$=resistance to heat transfer, s/m.
  $\Delta u$=difference in wind speed between elevations $z_2$ and $z_1$.
  For this calculation, considering that berms along the cultivation areas are approximately 10 cm high, it is assumed that the roughness height, $z_1$, is 1 cm or 0.01 m. This calculation method was used for the simulations in this application.

If water is static (not moving) then the following approach should be used to calculate heat transfer through the water.

$$Ra = \frac{g\beta(T_s - T_\infty)l^3}{v\alpha}$$

where properties of air are decided based on average fluid temperature $T_f=(T_S+T_\infty)/2$. The characteristic length l is defined as $$l = \frac{A}{P}$$

where A is the area, and P is the perimeter of the heat transfer surface.

For example, at cold air temperature $T_\infty$ of 15° C. and water temperature $T_S$ of 25° C., there is Ra=1.52×10$^{10}$. For $10^7 \leq Ra \leq 10^{11}$ there is
Nu=0.15Ra$^{1/3}$
According to the definition of the Nusselt number, there is $$Nu = \frac{hl}{k} = 372$$

From which the heat transfer coefficient is obtained as $$h = \frac{Nuk}{l} = 3.83 \, W/(m^2K)$$

It was assumed that the evaporation from an open raceway or basin is approximately the same as the reference evapotranspiration used for irrigation management, which is theoretically correct. Reference evapotranspiration values were obtained from the Arizona Meteorological Network, which calculates reference evapotranspiration with the ASCE modified Penman Equation. Evapotranspiration was adjusted downward by 10% to account for losses in ET due to water color or oil on the water surface. Water loss per unit area (kg) was multiplied by the adjusted latent heat of vaporization at the water temperature. Net long wave radiation was calculated based on the following equation:

$$Rnl=4.9*10^{-9}*(273.15+T_w)^{4}*(0.34-0.14*ea^{0.5})/24*1000$$

where ea is actual vapor pressure (kPa), and $R_{nl}$ is the net long wave radiation (kJ). This equation adjusts total net long wave radiation for humidity and cloud cover.

Solar radiation was calculated with AZMET hourly measured solar radiation. Albedo (percent reflection of sunlight) of algae water was assumed to be between 20%, which is in the same range as that used by AZMET to calculate evapotranspiration (23%).

Figure 7:
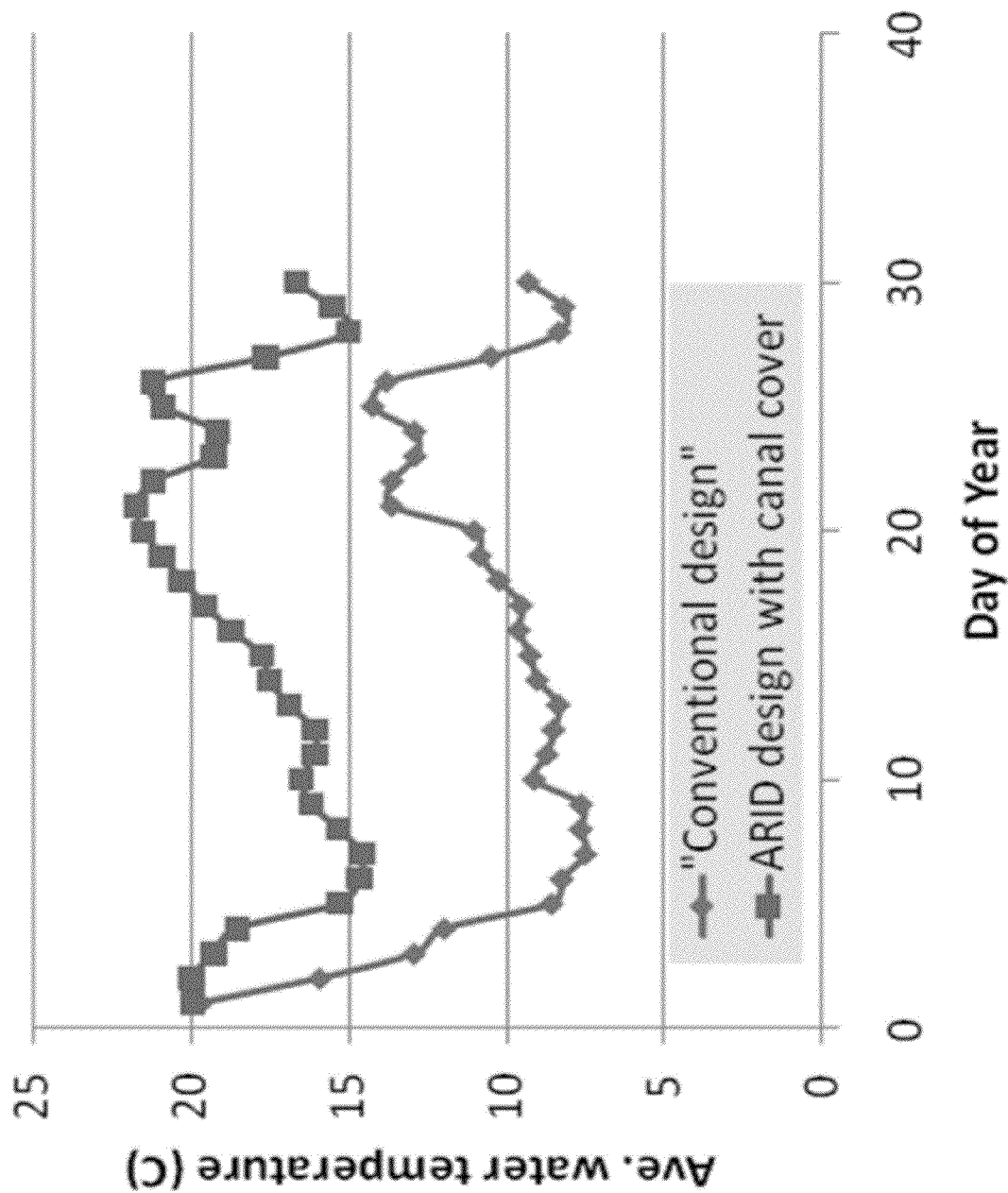
FIG. 7 is a graph showing simulation results comparing water temperatures of an ARID system of the type shown in FIG. 5 and a conventional open raceway design at midnight during January 2009 in Tucson, Ariz.
Figure 8:
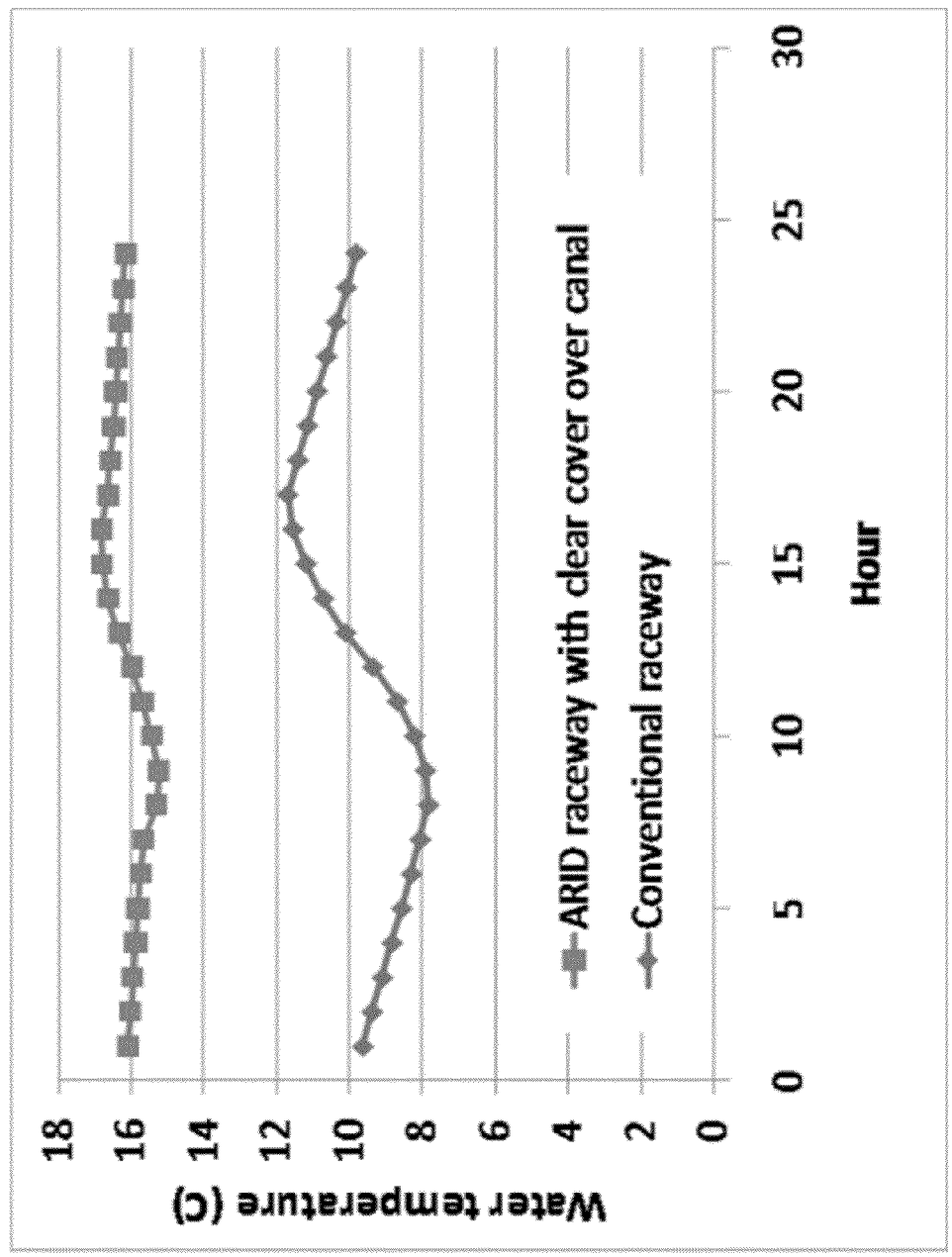
FIG. 8 is a graph showing simulated temperature of the ARID system and a conventional raceway on Jan. 16, 2009 in Tucson, Ariz.

An initial simulation based on changing water surface area showed that the water temperature could be maintained at approximately 19° C. during a typical winter month (January, 2009) with the algae ARID raceway system (FIG. 7). The water temperature in the ARID system during the simulation period, which began at the same temperature as the conventional raceway, was on average more than 8° C. warmer than the temperature in the conventional raceway design (FIG. 7) in the simulation. The simulation showed less diurnal change in algae temperature (FIG. 8) in the ARID system because the water has less exposure to the cold night air and less radiation to the night sky. The temperature remained at approximately the minimum level of the optimal range for part of the month. The dip in temperature could be eliminated by external heating during this period. It would also be reduced because of the fact that the soil would provide some thermal buffering. This was not accounted for in this simple model but is accounted for in the full ARID raceway model in Example 4.

Example 2

Comparison of Evaporation from Covered and Uncovered Systems

This example describes simulations comparing evaporation in a disclosed ARID system with and without a cover system.

Figure 9:
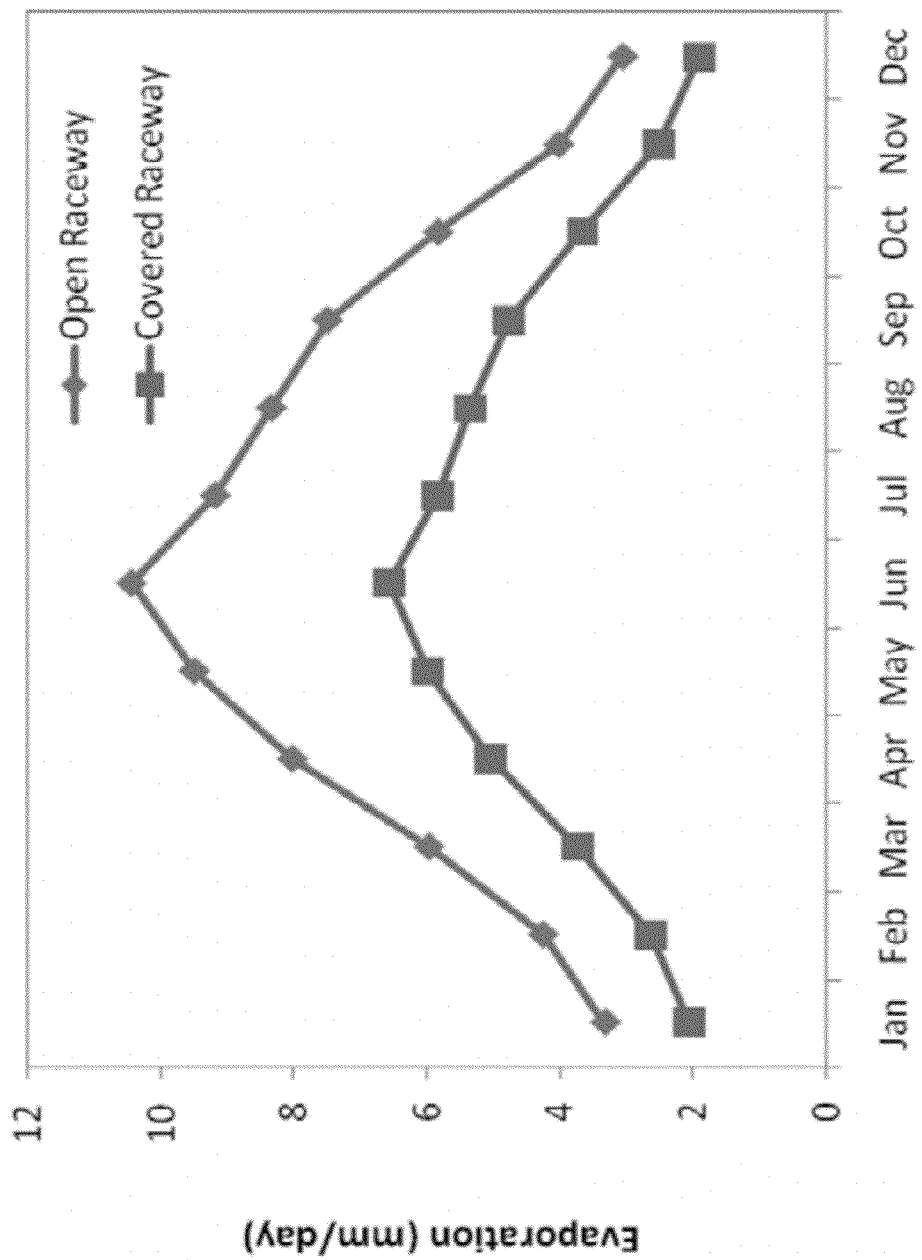
FIG. 9 is a graph showing simulated evaporation rates from open versus covered ARID systems of the type shown in FIG. 5 in Tucson, Ariz.

A comparison was made between the expected evaporation rate between a covered and uncovered ARID raceway system (of the type shown in FIG. 5 and with parameters as described in Example 1) in Southern Arizona. The evaporation rate of water from an open water surface per unit area was calculated using Penman-Monteith model (Reference ET) for Tucson, Ariz. For example, the daily water evaporation rate based on annual monthly average climatic data (AZMET average data) from an open raceway pond system located in Tucson, Ariz. would be around 6.63 mm/day (FIG. 9). This evaporation rate could be reduced by about 40% to 4.18 mm/day by covering the raceway pond with a low cost polyethylene greenhouse glazing material with 70% transmission (FIG. 9). This calculation was based on greenhouse evaporation calculation methods at the Controlled Environment Agriculture Center at the University of Arizona in Tucson, Ariz.

Example 3

Algae Growth in ARID Prototype

This example describes growth of algae in a prototype ARID system in Tucson, Ariz. in May-June 2010.

Figure 10:
FIG. 10 is a digital image of the 10 m×5 m prototype system.

The ARID raceway was constructed according to the design shown in FIGS. 1-4. The system had overall dimensions of 10 m×5 m with three cultivation areas having a slope of 1%. (1 m/100 m, or 10 cm fall over the 10 m length). A digital image of the system is provided in FIG. 10. The bottom of the cultivation areas and the collection area were lined with 30 mil thickness linear low density polypropylene (Aquafarm E-300, Colorado Lining International, Parker, Colo.). There were three water-filled tubes 15 cm in diameter (every 3 m) that backed up flow as it traveled down the cultivation areas. Drop between each water filled tube was approximately 3 cm, and average water depth was approximately 12 cm. Water-filled tubes extended across the basin (5 m) and they were held in place by shorter gravel-filled tubes placed behind the water-filled tube. Water was fed from a pipe with holes spaced at locations such that water flow into the basin caused eddies in the basin.

The system was inoculated with a 55 gallon drum of *Botryococcus braunii* algae (180 L) on day 1. The cell count in the inoculation barrel was not measured; however, if the initial cell count in the barrel was 10 million cells/ml, then the initial cell count on day 1 in the raceway with a total volume of 8000 L would have been 225,000 cells per ml. The water initially looked clear, but greenish, when cells were first added. Carbon dioxide was bubbled from a tank into the canal section during daylight hours and 2 cups of Peters fertilizer solution was added to the raceway at the time of inoculation. During algae culture 1 cup of Peters fertilizer solution was added to the raceway every 1-2 days. The culture was circulated using the pump for 9 am to 6 pm each day, and the culture was drained from the cultivation areas and stored in the collection area from 6 pm to 9 am.

On the first day after inoculation (day 2), the sump pump in the canal was barely visible at a depth of 1 m. Thus, in one day, the water had changed from clear to green and blocked the light. On the second day after inoculation (day 3), the sump pump was no longer visible at a depth of 1 m.

The first sample was collected on day 3 at 7:00 a.m. and counted with a hemacytometer and was 950,000 cells/ml. A second sample was collected at 4:00 p.m. on day 3, with a cell count of 1,320,000 cells/ml. In the first sample, no contamination was observed with very few cells motile, all small with only one aggregation, and a fair amount of inorganic particulates. In the second sample, two diatoms were observed and one colony of microcystis. A third sample was taken at 7:15 a.m. on day 4. The number of cells was 3,160,000 cells/ml. Thus, cell count more than doubled overnight.

The next cell count was conducted on day 11 at 6:00 p.m. There were 39,000,000 cells/ml. Thus, the number of cells increased approximately 12.5 times over a space of 6 days (from day 5 to day 11). This means that cells doubled more than once, but less than twice, per day in the tens of millions of cells range over the six day period. There were very few other organisms in the raceway beside the inoculated algae.

The harvest was conducted on day 11. Approximately 600 gallons (2000 L) of water was delivered to a conical tank. The algae were separated from the water by chemical settling. Harvested algae had a peanut butter consistency after drying. The water was not returned to the raceway in order to avoid contamination by chemicals used to harvest the algae. Extra water was added to the raceway from a local water source in order to replace the water lost to harvesting.

A second harvest of a similar amount of water was conducted on day 12. Extra water was also added to the raceway after this harvest. The cell count was low on day 12 (but not measured). It increased to 68 million cells per ml on day 19, after which the third and fourth harvests were taken. After these harvests, the cell count was measured as 17 million cells/ml on day 24. It increased to 48 million cells/ml on day 26 and 57 million cells/ml on day 29, after which harvests were collected. The penultimate harvest was conducted on day 31, when the algae concentration was 47 million cells/ml. At that time, the nutrients and $CO_2$ were turned off, and the entire system was harvested and emptied on days 34 and 36. Up until the time that nutrients and $CO_2$ were stopped the algae continued to grow at a rapid pace and looked very healthy during the entire period. The maximum cell count observed during this period, 68 million cells per ml, compared very favorably with the maximum laboratory cell count of 80 million cells/ml. The final sample was examined on day 33 had a low overall contamination level; with nearly no contaminants compared to algae cells. This shows that the ARID system had a low susceptibility to microbial contamination, as operated in central Arizona during May and June.

Example 4

Modeling of Effect of Soil Zones

Figure 11:
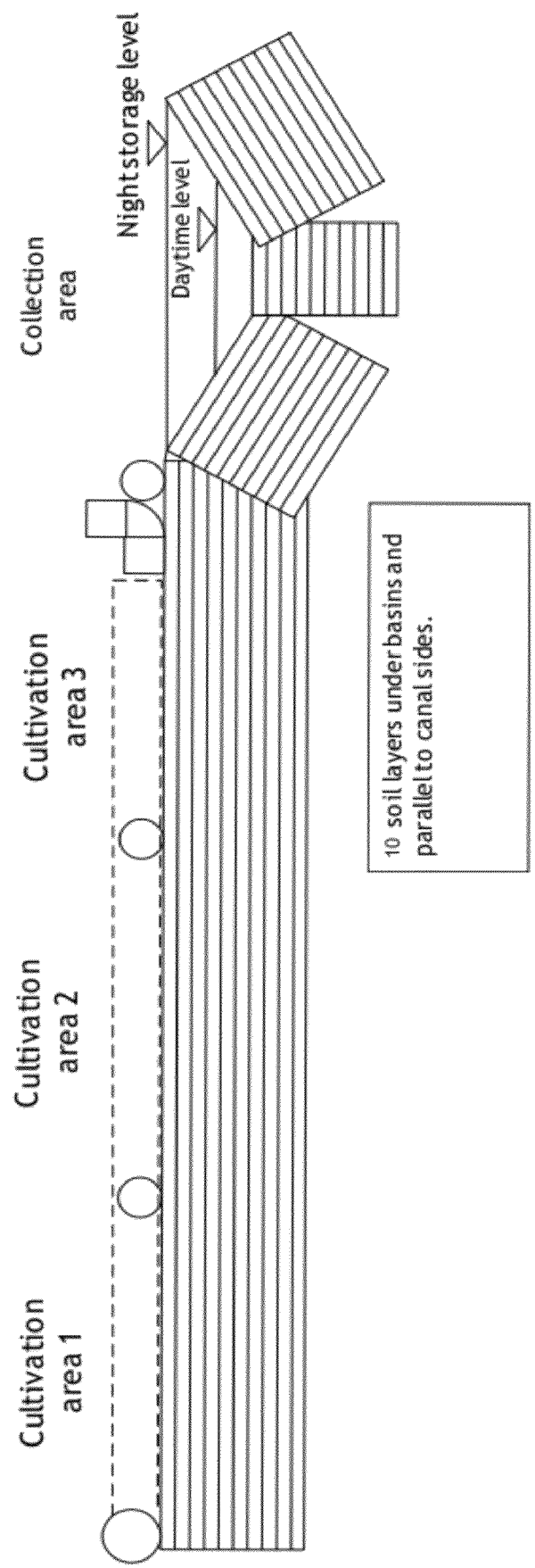
FIG. 11 is a diagram of the ARID system showing 10 soil layers under the bottom of the cultivation areas and the bottom and sides of the collection area.

A temperature model of the ARID system was developed. This model was a finite difference model written in Visual Basic for Applications. It included a simulation of 10 soil layers (referred to as zones in the figures) under the system as thermal storage, and water movement between cultivation areas and into and out of the canal. It also included the possibility of an insulating layer between the liner and the soil. Each of the cultivation areas and the collection area were modeled independently, but water and energy were transferred between cultivation areas and the collection area after each time step to reflect the fact that flow took place between areas. The layout of the model is shown in FIG. 11. In the simulation, cultivation areas were emptied at night and the collection area was emptied in the daytime. Each of the soil layers (each layer 5 cm depth) under cultivation areas and the collection area was assumed to have the following typical soil thermal properties:

Soil thermal conductivity: K=0.0002 kW/(m–K)
Soil heat capacity: C=0.8 kJ/kg K
Soil density: $\rho$=1500 kg/m3

Energy balance simulations were conducted with Arizona Meteorological Network (AZMET) hourly data from thirteen days before inoculation to day 13 of the culture (Apr. 28, 2010 to May 21, 2010). This was the period during which sensor measurements were collected. It included the periods before and after inoculation. The model drained water into the collection area at 6:00 p.m. and filled the cultivation areas at 9 a.m., which was the practice used with the prototype system described in Example 3. The thermal energy balance was based on the sensible heat flux, net long wave radiation, evaporation and associated latent heat of vaporization, and solar radiation described in Example 1.

Solar radiation was calculated with AZMET hourly measured solar radiation. Albedo of water with algae was estimated as 20%. Thus, it was assumed that 80% of solar radiation was absorbed by water in basins.

Figure 12:
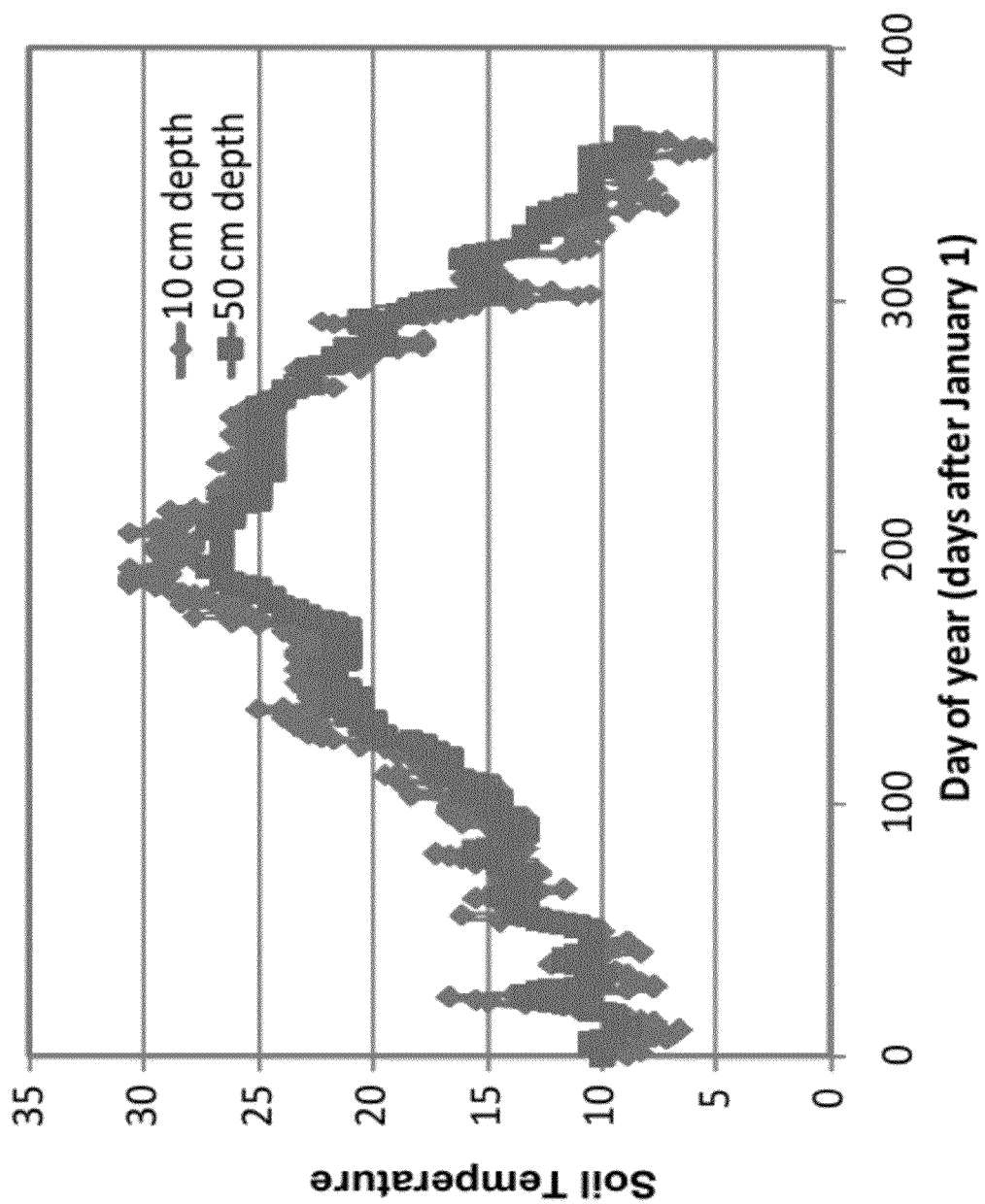
FIG. 12 is a graph showing soil temperature at 10 cm and 50 cm depths below soil surface at Tucson AZMET weather station located 100 meters from the prototype system.

Average soil temperature at a depth of 50 cm at the Tucson AZMET weather station, which is under turf is shown in FIG. 12. The weather station was approximately 100 meters from the ARID raceway prototype. The winter temperatures drop to approximately 6° C. and the summer temperatures rise to approximately 30° C. These temperatures are outside the optimal temperature range of many species of algae. However, over a large algae cultivation area, mean monthly soil temperatures should adjust to the mean monthly algae water temperature. In the following simulations, the soil temperature was set by running the simulation and observing the equilibrium water and soil temperature after two weeks of simulation. Then the base soil temperature at the bottom of the simulation zone (zone 10), as well as the initial soil and water temperature values, were set at this equilibrium temperature, and the model was rerun for the period of simulation.

Figure 13:
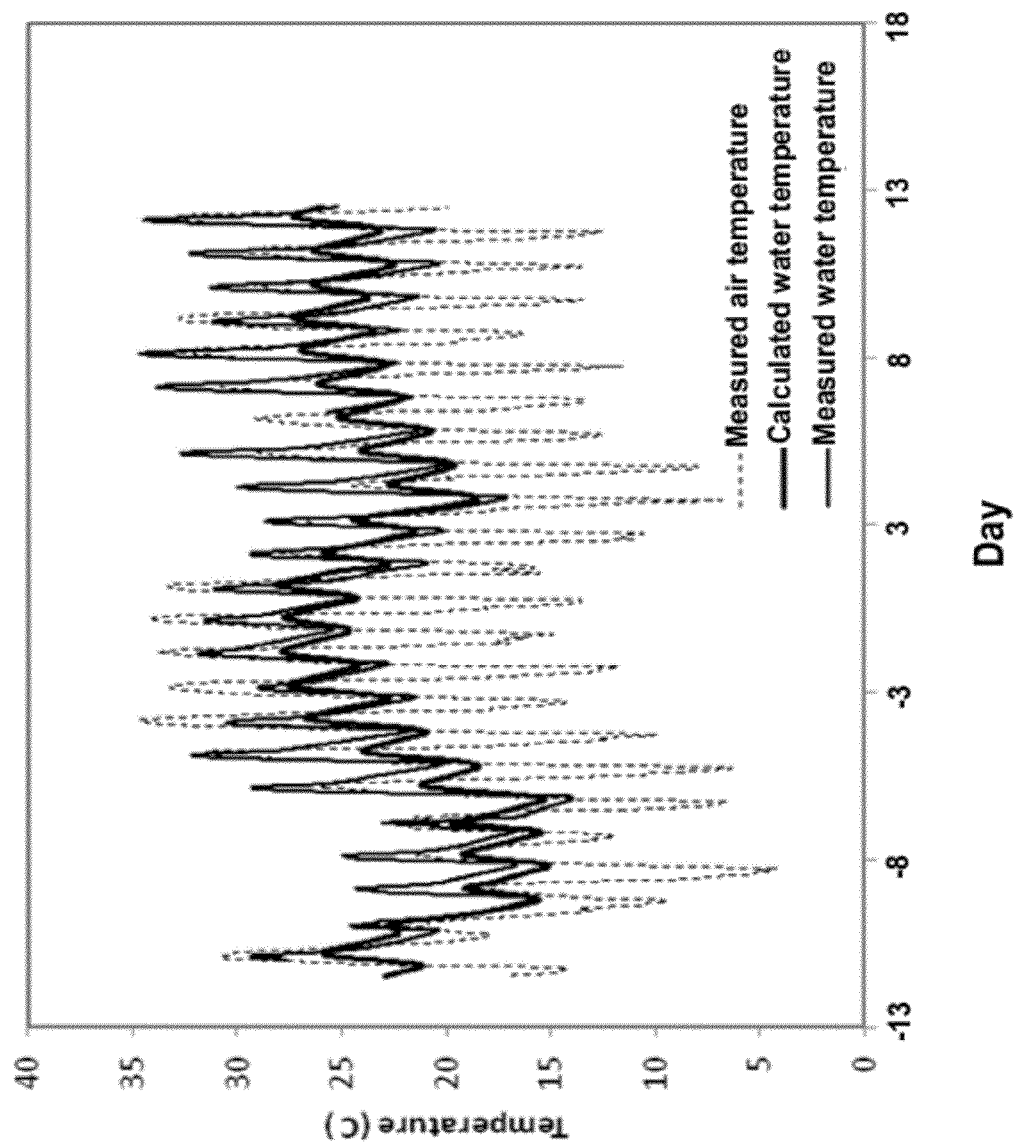
FIG. 13 is a graph showing measured water temperature in the prototype system and simulation of the water temperature using AZMET air temperature, wind speed, humidity, and solar radiation data immediately before and during the period of algae production. The inoculum was added to the system on Day 1.

The model results compared very well with the observed temperature in the collection area, which was measured with a thermocouple. A graph of AZMET air temperature, simulated collection area temperature, and measured collection area temperature is shown in FIG. 13. A drop in measured temperature below the simulated temperature was observed at the end of the simulation. This drop was due to the addition of colder well water to replace harvested water. It is also likely that this is the cause of the drop at the time of inoculation (days 1-3) since this was the inoculation period and new water would have been added to bring the raceway to a full condition prior to inoculation. However, this addition of water was not recorded. The high peaks in the measured data are caused by the influence of sunlight on thermocouples; however, the minimum values collected at night are accurate. The diurnal changes in simulated (calculated) water temperature are in the range of those measured with a hand-held instrument. The comparison with field data shows that the model provides a very accurate simulation of raceway temperature. Model parameters were not intentionally adjusted in order to make the model fit the curve.

Figure 14:
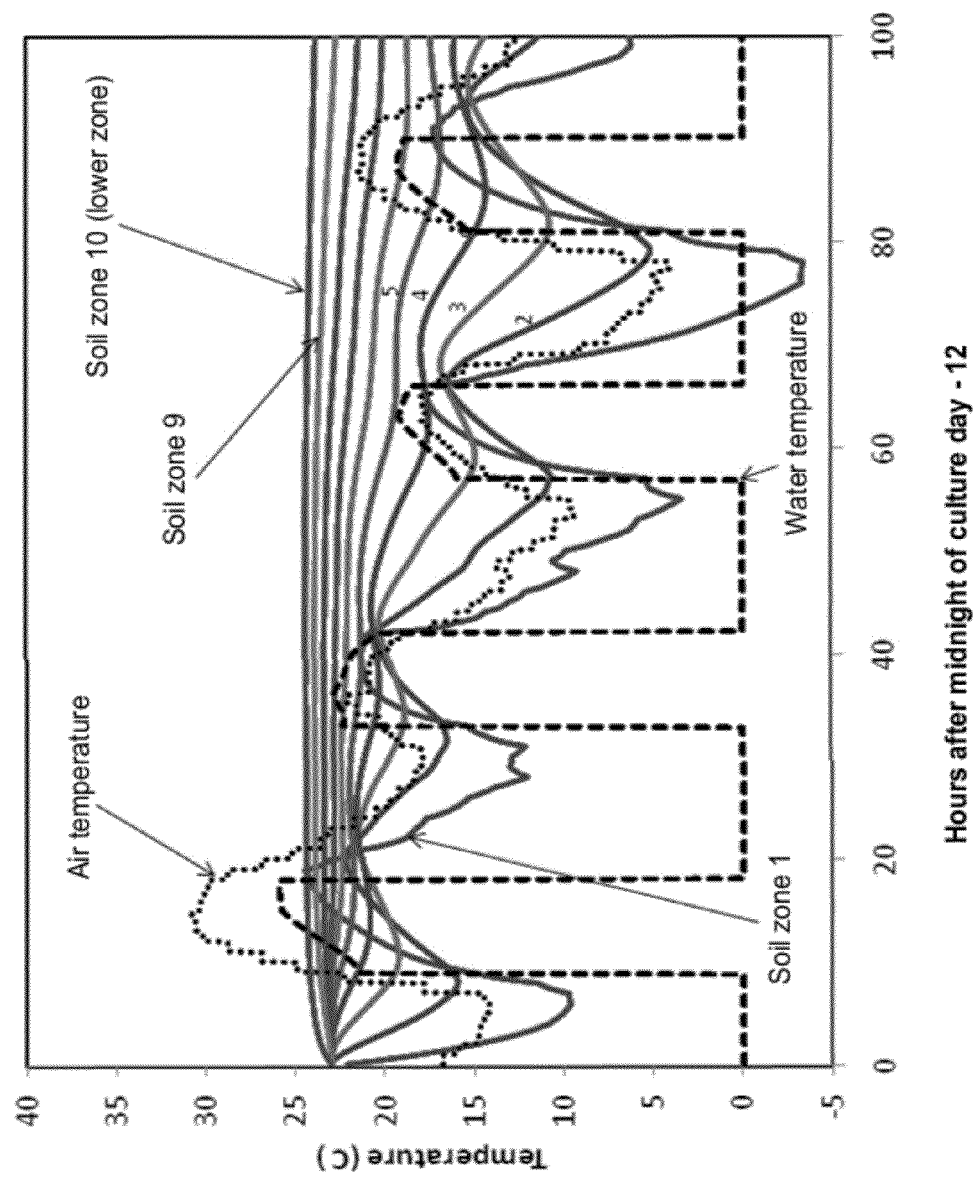
FIG. 14 is a graph showing simulated water and soil temperatures in each soil layer for cultivation area 1 shown in FIG. 11 for four days after midnight on day-12.

Simulated temperature in each soil layer and in the water for cultivation area 1 during the first four days of the simulation are shown in FIG. 14. In order to show more detail, only four days are shown. Water was emptied from the cultivation areas at night, which is why the temperature drops to zero (there is no water). Soil temperatures in lower layers are relatively constant, which is expected since the earth acts as a buffer.

Figure 15:
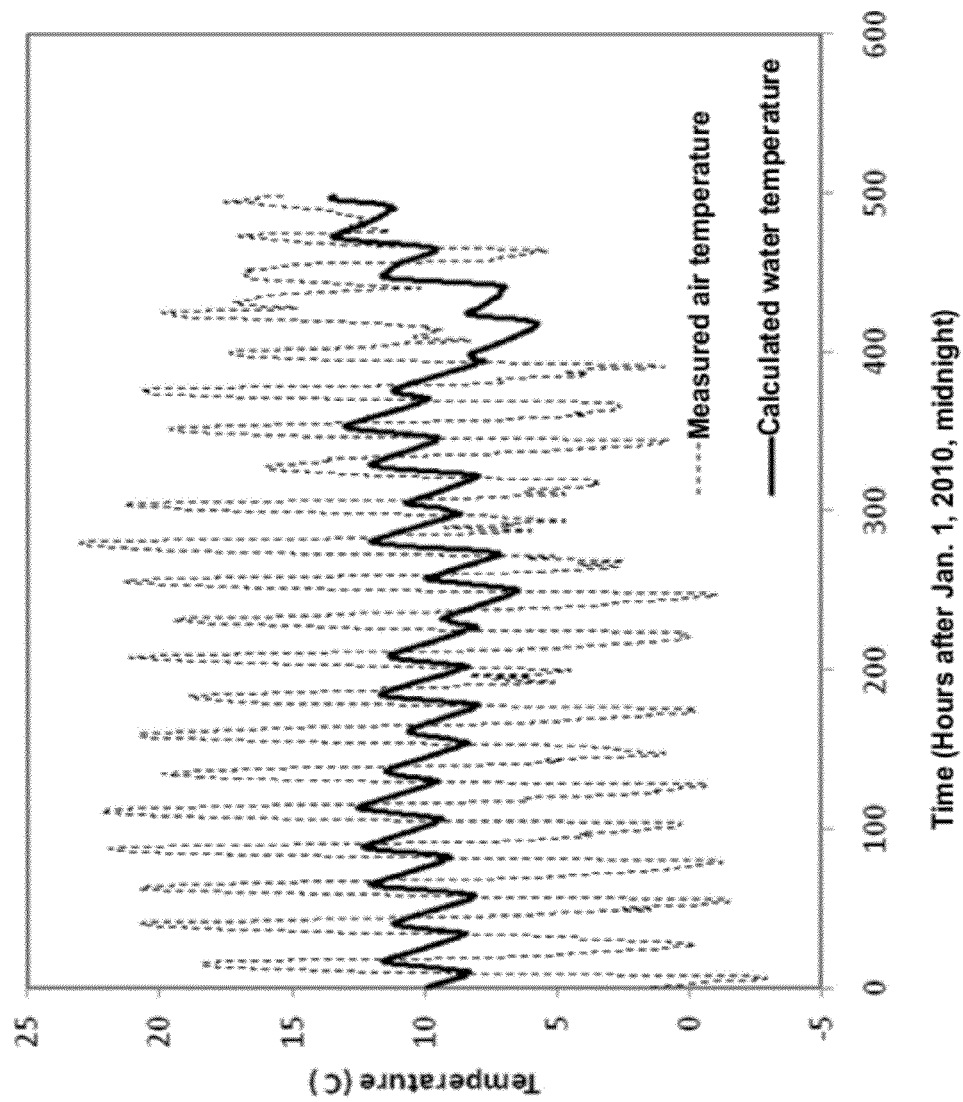
FIG. 15 is a graph showing a simulation of cultivation area water temperature in January 2010 in Tucson, Ariz. with no cover over the collection area or cultivation areas and no insulation or radiant barrier under the cultivation areas. Basal soil temperature and initial water temperature in the simulation were 10° C.
Figure 16:
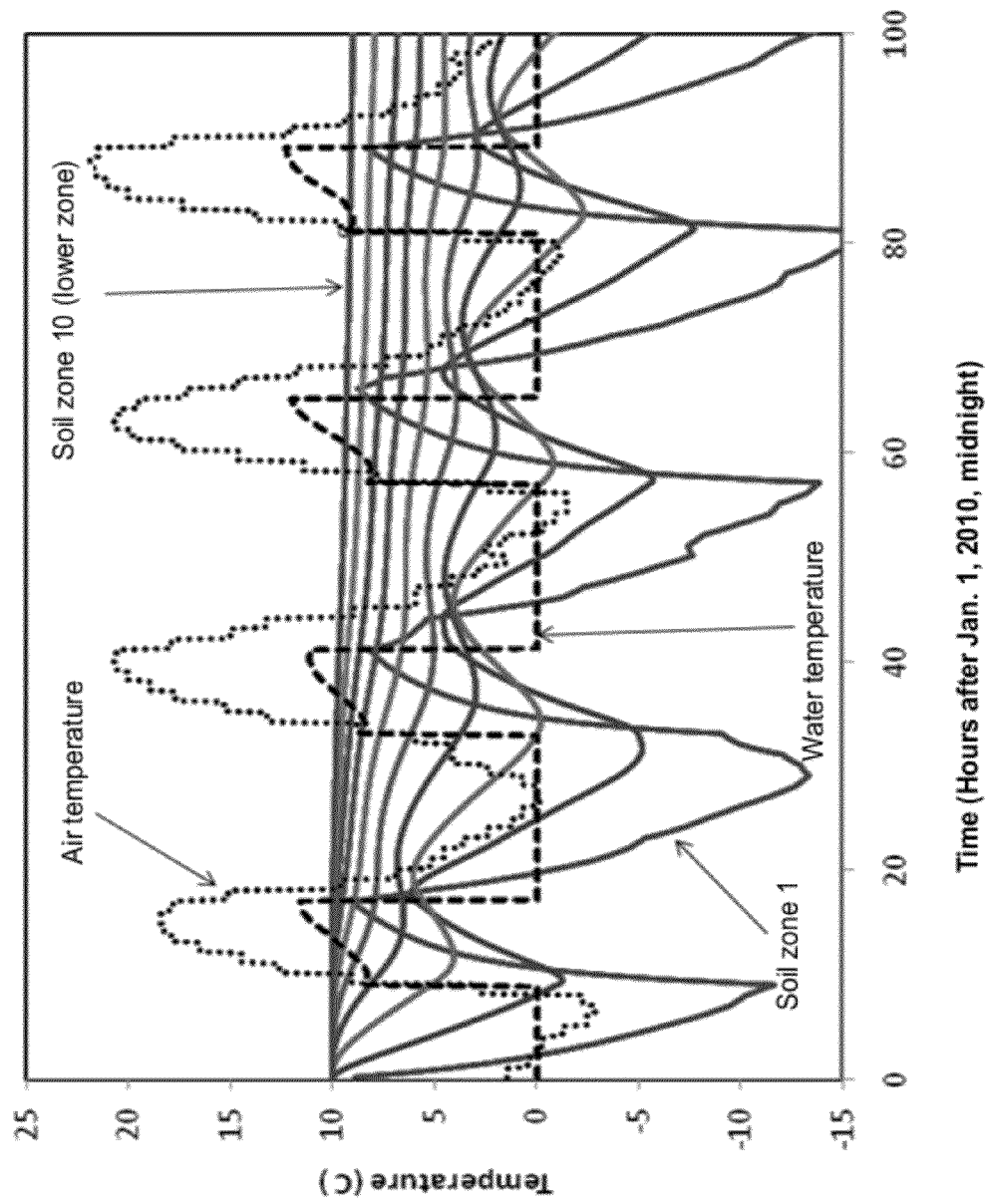
FIG. 16 is a graph showing simulated water and soil temperatures for four days after midnight on Jan. 1, 2010, in Tucson, Ariz., for cultivation area 1 shown in FIG. 11 for the simulation shown in FIG. 15.

After the model was shown to be accurate as shown in FIG. 13, simulations were conducted for winter temperatures during January, 2010. With uninsulated cultivation areas and an uncovered collection area in winter, with resultant unrestricted long wave radiation at night, the soil temperatures and water temperature had an equilibrium temperature of approximately 10° C. (FIG. 15). This simulation was run with a simulation of soil temperatures down to 50 cm with a basal soil temperature below this depth fixed at 10° C. The model was run with 10 soil layers (each layer 5 cm depth) under cultivation areas and the collection area (FIG. 11). Corresponding soil temperatures during the first 4 days of 2010 are shown in FIG. 16.

Figure 17:
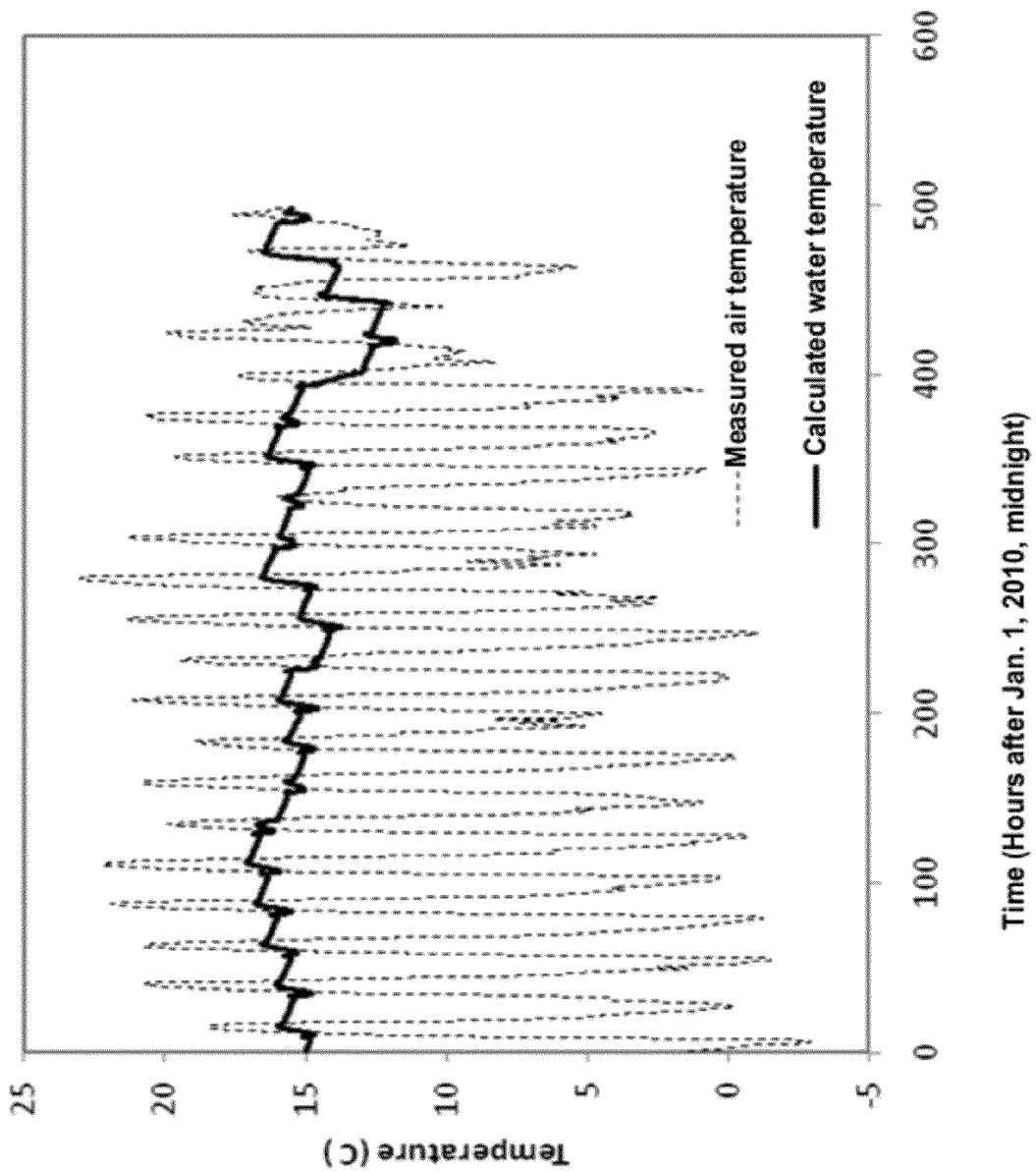
FIG. 17 is a graph showing a simulation of cultivation area water temperature in January 2010 in Tucson, Ariz. with a transparent cover over the collection area or and no insulation or radiant barrier under the cultivation areas. Basal soil temperature and initial water temperature in the simulation were 15° C.

The next simulation included a clear cover (for example, Mylar®) over the collection area. It was assumed that the cover reduced radiation (10% of normal), sensible heat (10% of normal), evaporation (20% of normal), and allowed full sunlight (80% of normal penetrated the water). The bottom of the cultivation areas were only covered with the liner, with no insulation or radiant barrier. The equilibrium temperature was approximately 15° C. in this case (FIG. 17).

The next simulation included the previous conditions but placed a one inch polystyrene board below the liner in the cultivation areas. The following parameters of a polystyrene board were used in the upper soil layer.

Polystyrene thermal conductivity: K=0.00008 kW/(m–K)
Polystyrene heat capacity: C=1.3 kJ/kg K
Polystyrene density: $\rho$=100 kg/m3
Thickness: 2.5 cm.

Figure 18:
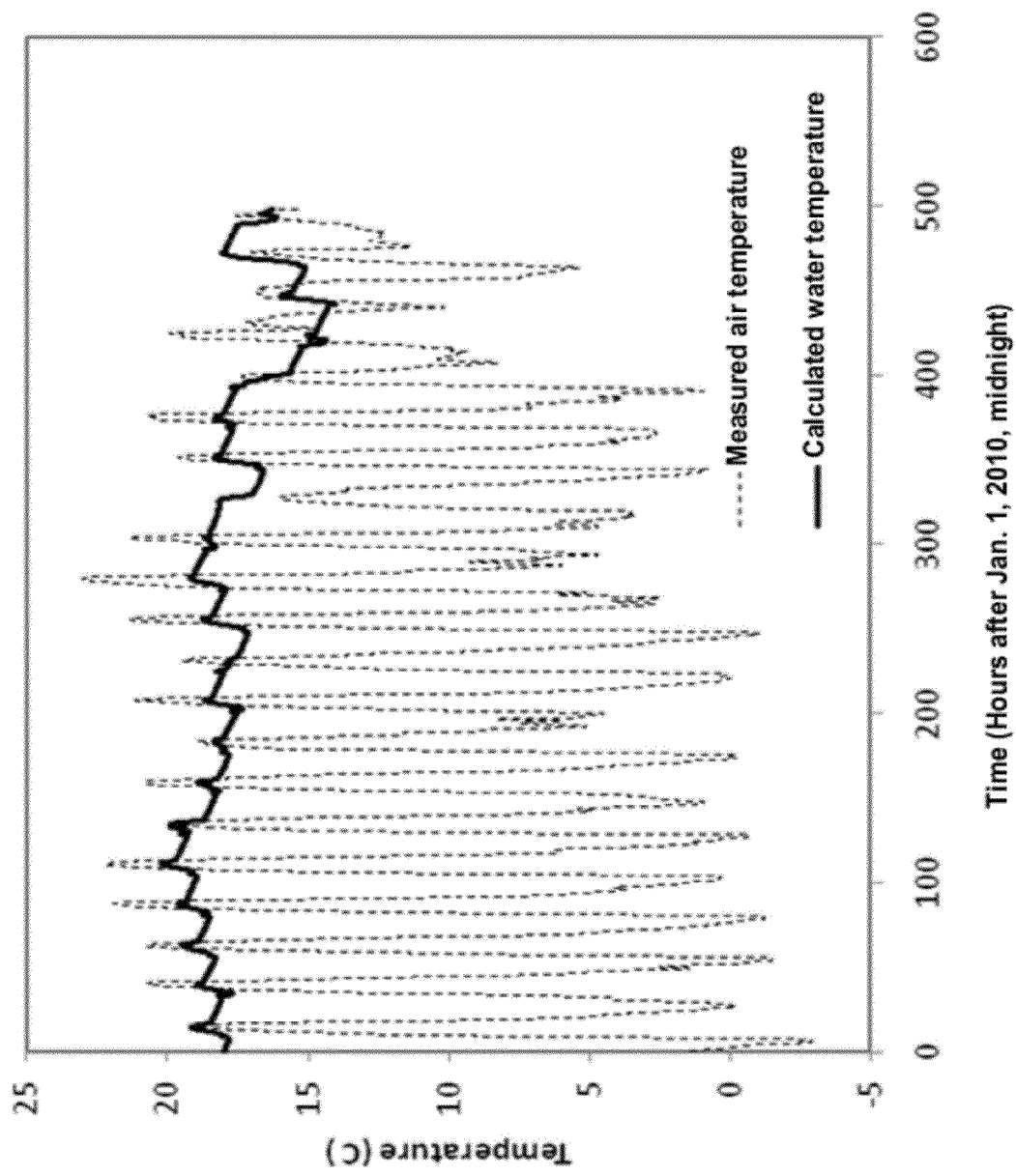
FIG. 18 is a graph showing a simulation of cultivation area water temperature in January 2010 in Tucson, Ariz. with a transparent cover over the collection area and one inch extruded polystyrene under the liner in the cultivation areas. Basal soil temperature and initial water temperature in the simulation were 18° C.

The presence of the polystyrene board under the cultivation areas resulted in an equilibrium temperature equal to 18° C. (FIG. 18).

The next simulation included a radiant barrier (foil or other reflective surface) between the liner and the soil in the cultivation areas. In this case, when the cultivation area is filled with water, there will be efficient heat transfer between the water and the soil. However, the liner can be lifted at night after the water is drained (for example by injecting air). This air gap will prevent sensible heat transfer at night from the atmosphere to the soil. The liner can be lifted by injecting air and creating air pressure beneath the liner with a pneumatic device or with strategically placed objects that cause the linear to lift at night. The following calculation assumed that there was a 1 inch air gap between the liner and foil on the soil surface.

The selection of the Rayleigh number equation is based on a characteristic length, H, of the basins of 3.45 m and a gap between the liner and reflective surface equal to 0.026 m (2.5 cm). For this calculation, it was assumed that the temperature difference between the liner and the reflective barrier is 20° C.

$$H/L = 3.45/0.026 = 130 \rightarrow 500H/L = 66,000$$

The Rayleigh number, Ra, is 11,000 and is less than 500H/L, and the Nusselt number should be calculated as follows:

$$Nu = 1 + Ra/720 \,(130) = 1.11$$
$$h = \frac{1.11(0.0242)}{0.026} = 1.0 \; W/(m^2 K)$$

Figure 19:
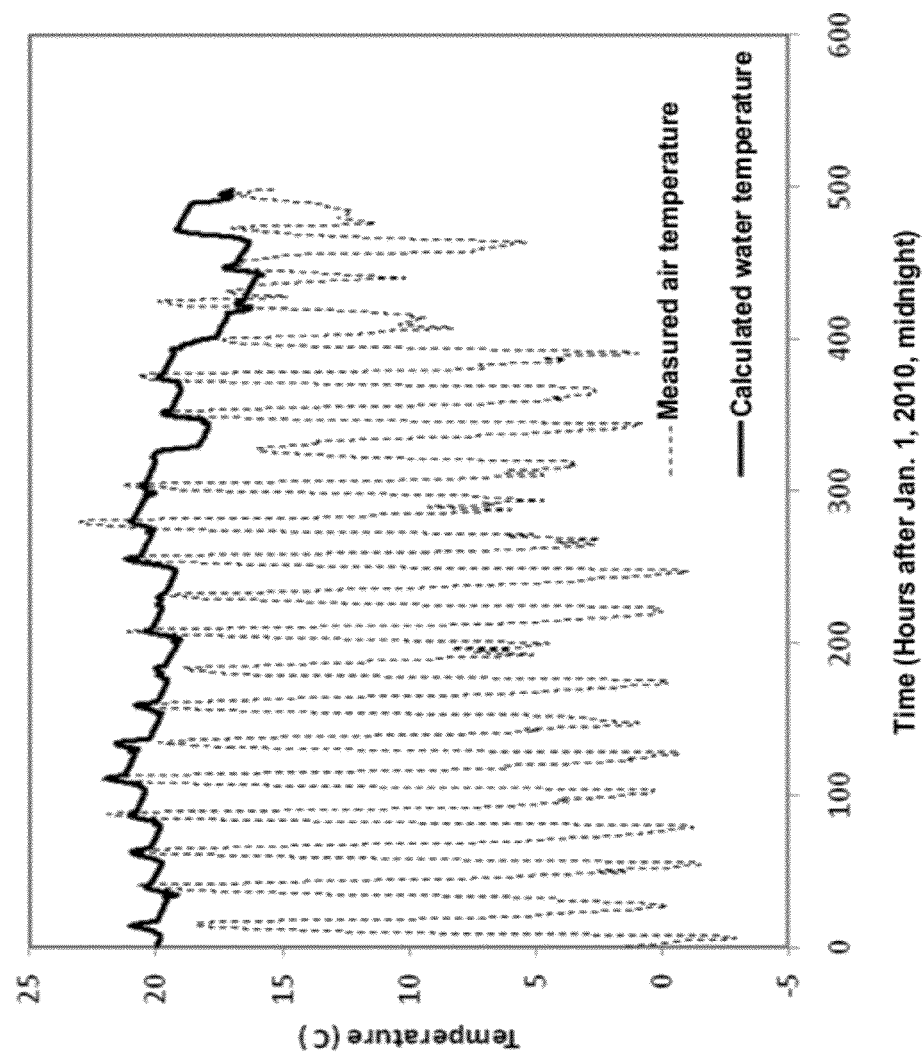
FIG. 19 is a graph showing a simulation of cultivation area water temperature in January 2010 in Tucson, Ariz. with a transparent cover over the collection area and a radiant barrier and one inch air gap under the liner in the cultivation areas. Basal soil temperature and initial water temperature in the simulation were 20° C.
Figure 20:
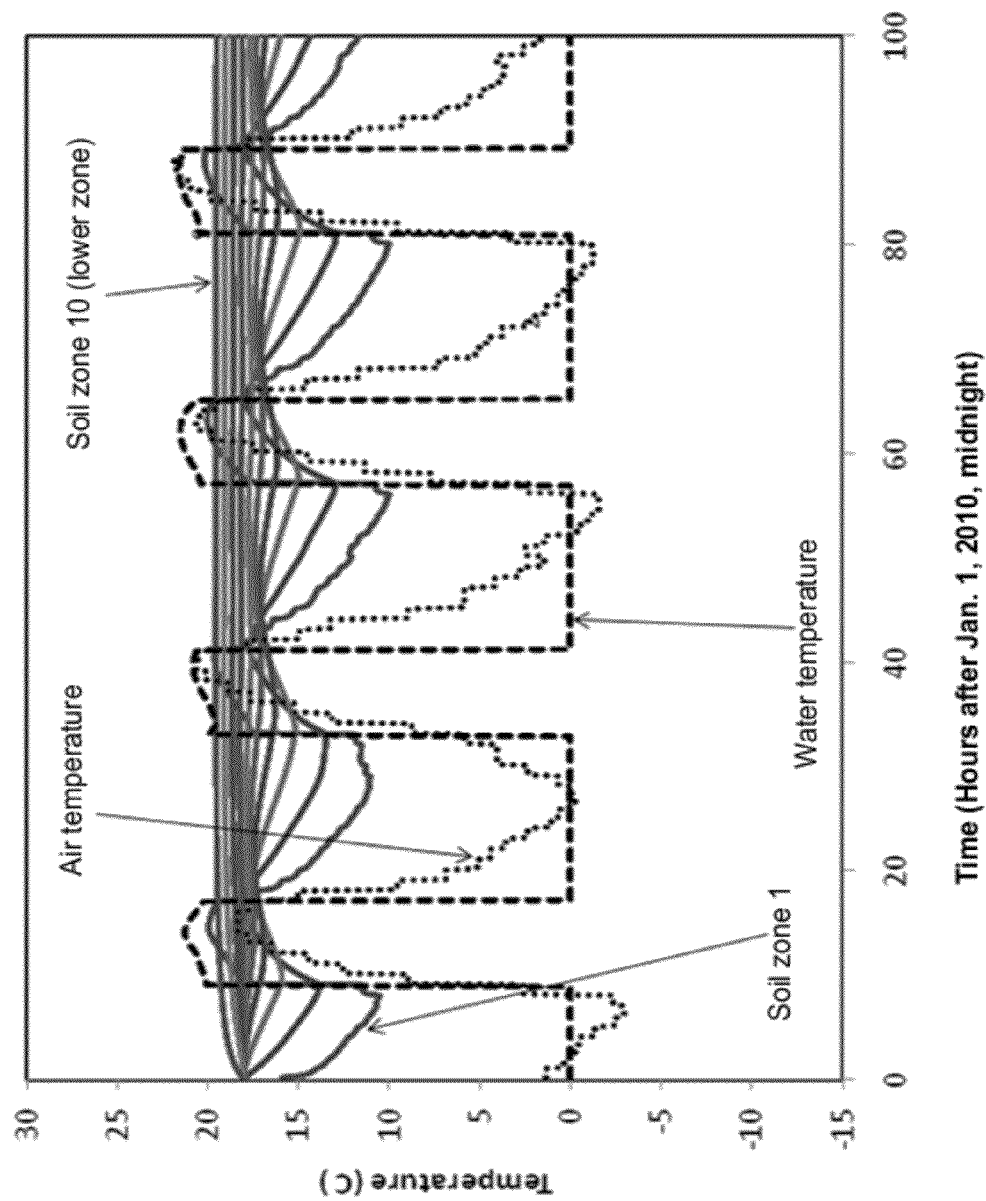
FIG. 20 is a graph showing simulated water and soil temperatures for four days midnight on Jan. 1, 2010, Tucson, Ariz., for cultivation area 1 shown in FIG. 11 and for simulation shown in FIG. 19.

Thus, the convective heat transfer coefficient used in the model was 0.001 kW/(m² K). This is much lower than the heat transfer across the reflective barrier, across the liner, or from the liner to the atmosphere. Thus, the low convective heat transfer coefficient across the air gap was used in the model. It was also assumed that the radiant barrier completely blocks radiant heat transfer. It was assumed that the liner is at atmospheric temperature since heat transfer from the atmosphere to the liner will be much less restricted than heat transfer from the soil to the liner. Thus, the model at night, when the cultivation areas were emptied included soil in the surface layer, no radiation, and sensible heat transfer based on a sensible heat transfer coefficient of 0.001 kW/(m² K). The simulation showed that temperature remains above 20° C. for most of January (FIG. 19). Corresponding soil temperatures for the first four days of the year are shown in FIG. 20.

Figure 21:
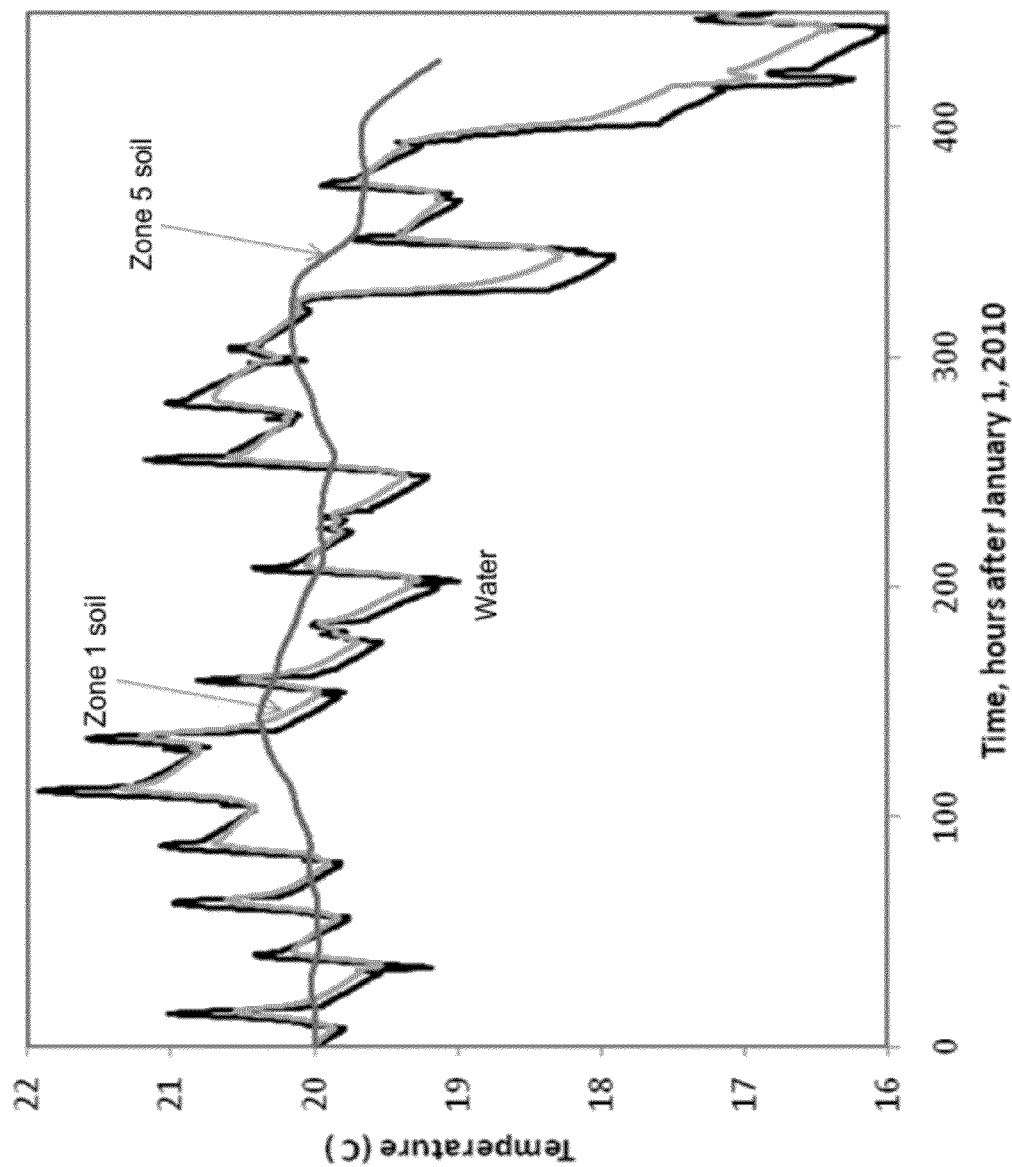
FIG. 21 is a graph showing simulated water and soil temperatures in the collection area for January, 2010, Tucson, Ariz.

The collection area helped to prevent water temperature decrease during the cold period of the month. This is shown in FIG. 21, which shows simulated collection area soil temperature in layers 1 and 5. Note that heat was moving from the soil to the water in the canal based on the temperature gradient. Thus, the soil thermal mass below the canal helped to regulate water temperature during temporary spells of low temperature or storms.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A system for aquaculture, comprising: n
   a plurality of cultivation areas comprising at least a first cultivation area and a second cultivation area, each cultivation area comprising:
   an upper end;
   a lower end, wherein the upper end and the lower end are substantially parallel; and
   a bottom surface comprising a liner;
   a collection area below the lower end of at least one of the plurality of cultivation areas;
   a pump for returning the culture from the collection area to the upper end of at least one of the plurality of cultivation areas; and
   at least one delivery device for providing gas and/or nutrients to the culture;
   wherein the lower end of the first cultivation area is separated from the upper end of the second cultivation area by a flexible barrier running an entire length between the cultivation areas and connected at each end thereof, wherein the flexible barrier is higher than a water surface elevation in use, wherein the flexible barrier is maintained in position by one or more backstops to prevent the barrier from shifting, and wherein the flexible barrier comprises at least one flow pathway for flow of the culture from the first cultivation area to the second cultivation area or from the second cultivation area to the collection area.

2. The system of claim 1, wherein each of the cultivation areas comprises a downward slope from the upper end to the lower end.

3. The system of claim 1, wherein at least one of the plurality of cultivation areas and/or the collection area are adjacent to the ground.

4. The system of claim 3, further comprising a low thermal conductivity material between at least one of the plurality of cultivation areas and/or the collection area and the ground.

5. The system of claim 1, wherein the upper end of each of the plurality of cultivation areas are adjacent to one another.

6. The system of claim 1, wherein the lower end of the first cultivation area is substantially parallel with the upper end of the second cultivation area.

7. The system of claim 1, further comprising at least one intervening cultivation area between the first and the second cultivation areas.

8. The system of claim 1, further comprising a canal, wherein the canal is substantially parallel to the upper end of at least one of the cultivation areas, and wherein the culture is introduced into the upper end of at least one of the plurality of cultivation areas by exiting from the canal.

9. The system of claim 8, wherein the canal comprises at least one opening for exit of the culture to the at least one cultivation area.

10. The system of claim 1, wherein the bottom of at least one of the plurality of the cultivation areas comprises at least one flow disturbance means.

11. The system of claim 10, wherein the flow disturbance means comprises at least one baffle or rib structure.

12. The system of claim 1, further comprising a pipe connected to the pump, wherein the pipe carries the culture to the canal.

13. The system of claim 1, further comprising a cover for at least one of the plurality of cultivation areas, the collection area, the canal, or a combination of two or more thereof.

14. A method for regulating water temperature of an aquaculture comprising:
   circulating the culture through the system of claim 1; and
   storing the culture in the collection area, at least one of the plurality of cultivation areas, or a combination thereof for at least a portion of a 24 hour period, thereby regulating the water temperature.

15. The method of claim 14, wherein the water temperature is increased by circulating the culture through the system in the presence of solar radiation.

16. The method of claim 14, wherein the water temperature is decreased by circulating the culture through the system during a period of lower relative solar radiation.

17. The method of claim 14, wherein the water temperature is maintained at or above a minimum temperature by storing the culture in the collection area.

18. The method of claim 14, wherein the water temperature is maintained at or below a maximum temperature by storing the culture in one or more of the plurality of cultivation areas.

19. The method of claim 14, wherein circulating the culture through the system comprises a flow rate of about 0.1 m/min to about 2 m/min.

20. The method of claim 14, wherein the depth of the culture in the plurality of cultivation areas is about 10-15 centimeters during circulation.

21. The method of claim 14, wherein the depth of the culture in the collection area is about 50 centimeters during circulation of the culture and wherein the depth of the culture in the collection area is about 150 centimeters during storage of the culture.

22. The method of claim 14, further comprising covering the collection area and/or at least one of the plurality of cultivation areas.

23. The method of claim 14, wherein the water temperature is about 15° C. to about 35° C.

* * * * *

UNITED STATES PATENT AND TRADEMARK OFFICE
CERTIFICATE OF CORRECTION

PATENT NO. : 8,245,440 B2
APPLICATION NO. : 12/824106
DATED : August 21, 2012
INVENTOR(S) : Ryan et al.

It is certified that error appears in the above-identified patent and that said Letters Patent is hereby corrected as shown below:

In the Claims:

Column 25, line 60 (claim 1), "aquaculture, comprising: n" should read --aquaculture, comprising:--.

Signed and Sealed this
Twelfth Day of March, 2013

Teresa Stanek Rea
*Acting Director of the United States Patent and Trademark Office*